United States Patent
Tsukagoshi et al.

(10) Patent No.: US 10,540,764 B2
(45) Date of Patent: Jan. 21, 2020

(54) MEDICAL IMAGE CAPTURING APPARATUS AND METHOD

(71) Applicant: Toshiba Medical Systems Corporation, Otawara-shi (JP)

(72) Inventors: Shinsuke Tsukagoshi, Nasushiobara (JP); Takahiro Goto, Utsunomiya (JP); Go Mukumoto, Obu (JP)

(73) Assignee: Canon Medical Systems Corporation, Otawara-shi (JP)

( * ) Notice: Subject to any disclaimer, the term of this patent is extended or adjusted under 35 U.S.C. 154(b) by 340 days.

(21) Appl. No.: 15/590,594

(22) Filed: May 9, 2017

(65) Prior Publication Data

US 2017/0323447 A1 Nov. 9, 2017

(30) Foreign Application Priority Data

May 9, 2016 (JP) .................................. 2016-094077
May 1, 2017 (JP) .................................. 2017-091251

(51) Int. Cl.
*G06T 7/11* (2017.01)
*G06T 7/00* (2017.01)
*G16H 50/50* (2018.01)

(52) U.S. Cl.
CPC ............ *G06T 7/0012* (2013.01); *G16H 50/50* (2018.01)

(58) Field of Classification Search
CPC ............ A61B 6/04; A61B 6/032; A61B 6/467; A61B 6/469; A61B 6/544; A61B 6/545; A61B 6/00; A61B 6/03; A61B 6/5217; A61B 6/5205; A61B 6/481; A61B 6/4035; A61B 6/465; G06T 7/11; G06T 11/60; G06T 7/00; G06T 2207/10081;
(Continued)

(56) References Cited

U.S. PATENT DOCUMENTS 8,467,495 B2 * 6/2013 Okada .................... A61B 6/022
378/151
2008/0063136 A1 3/2008 Ohyu et al.
2015/0297157 A1 * 10/2015 Mukumoto ........... A61B 6/5205
378/15

FOREIGN PATENT DOCUMENTS

JP 2004-290570 10/2004
JP 2007-181623 7/2007
(Continued)

*Primary Examiner* — Duy M Dang
(74) *Attorney, Agent, or Firm* — Oblon, McClelland, Maier & Neustadt, L.L.P.

(57) ABSTRACT

A medical image capturing apparatus according to an embodiment includes image generation circuitry, detection circuitry, diagnosis support processing circuitry, setting circuitry, and imaging control circuitry. The image generation circuitry generates image data of a subject. The detection circuitry detects each of a plurality of parts of the subject in the image data generated as a positioning image. The diagnosis support processing circuitry executes diagnosis support processing corresponding to a predetermined part with regard to a region corresponding to the predetermined part of the subject detected. The setting circuitry sets an imaging condition of main imaging with respect to a part in which a lesion site is specified as a processing result of the diagnosis support processing. The imaging control circuitry controls an imaging mechanism to perform imaging with regard to an imaging region including the part in which the lesion site is specified based on the imaging condition.

20 Claims, 15 Drawing Sheets

(58) Field of Classification Search
CPC ......... G06T 2207/30096; G06T 7/0012; G06T 7/35; G06T 1/00; G06T 11/00; G06T 11/003; G06T 11/008; G16H 50/50; H05G 1/64

See application file for complete search history.

(56) References Cited

FOREIGN PATENT DOCUMENTS

| | | |
|---|---|---|
| JP | 2008-11905 | 1/2008 |
| JP | 2008-12171 | 1/2008 |
| JP | 2008-12229 | 1/2008 |
| JP | 2008-67851 | 3/2008 |

* cited by examiner

FIG.5

| IDENTIFI-CATION CODE | COORDINATES | | |
|---|---|---|---|
| | POSITIONING | SCAN | |
| | | NON-CONTRAST PHASE | CONTRAST PHASE |
| C1 | (x1, y1, z1) | (x'1, y'1, z'1) | (x'1, y'1, z'1) |
| C2 | (x2, y2, z2) | (x'2, y'2, z'2) | (x'2, y'2, z'2) |
| C3 | (x3, y3, z3) | (x'3, y'3, z'3) | (x'3, y'3, z'3) |
| C4 | (x4, y4, z4) | (x'4, y'4, z'4) | (x'4, y'4, z'4) |
| C5 | (x5, y5, z5) | (x'5, y'5, z'5) | (x'5, y'5, z'5) |
| C6 | (x6, y6, z6) | (x'6, y'6, z'6) | (x'6, y'6, z'6) |
| C7 | (x7, y7, z7) | (x'7, y'7, z'7) | (x'7, y'7, z'7) |
| C8 | (x8, y8, z8) | (x'8, y'8, z'8) | (x'8, y'8, z'8) |
| C9 | (x9, y9, z9) | (x'9, y'9, z'9) | (x'9, y'9, z'9) |
| C10 | (x10, y10, z10) | (x'10, y'10, z'10) | (x'10, y'10, z'10) |
| ⋮ | ⋮ | ⋮ | ⋮ |
| C31 | | | (x'31, y'31, z'31) |
| C32 | | | (x'32, y'32, z'32) |
| C33 | | | (x'33, y'33, z'33) |
| C34 | | | (x'34, y'34, z'34) |
| ⋮ | ⋮ | ⋮ | ⋮ |

FIG.11

[HIGH-DEFINITION PLAN]
COLLECTION THICKNESS: ×××
D-FOV: ×××
kV: ×××
mA: ×××
C-FOV: ×××
RECONSTRUCTION CONDITION: ×××

SET   CANCEL

MEDICAL IMAGE CAPTURING APPARATUS AND METHOD

CROSS-REFERENCE TO RELATED APPLICATIONS

This application is based upon and claims the benefit of priority from Japanese Patent Application No. 2016-094077, filed on May 9, 2016 and Japanese Patent Application No. 2017-091231, filed on May 1, 2017; the entire contents of which are incorporated herein by reference.

FIELD

Embodiments relate to a medical image capturing apparatus and method.

BACKGROUND

Conventionally, in an examination using an X-ray CT apparatus (CT: Computed Tomography), a computer aided diagnosis (CAD) process for detecting a lesion site using a predetermined support diagnosis algorithm for a reconstructed image of a subject may be executed in some cases. In such a case, a radiologist interprets the reconstructed image with reference to a result of the CAD process.

BRIEF DESCRIPTION OF THE DRAWINGS

FIG. 5 is a diagram for description of an example part detection processing by the detection function according to the first embodiment;

FIG. 11 is a diagram (2) for description of the first embodiment;

DETAILED DESCRIPTION

Hereinafter, embodiments of a medical image capturing apparatus and method will be described in detail with reference to accompanying drawings. Hereinafter, a medical information processing system including an X-ray CT (Computed Tomography) apparatus will be described as an example. In a medical information processing system 100 illustrated in FIG. 1, only one server apparatus and one terminal apparatus are illustrated. However, in practice, it is possible to further include a plurality of server apparatuses and terminal apparatuses. Further, the medical information processing system 100 may include a medical image diagnostic apparatus such as an X-ray diagnostic apparatus, an MRI (Magnetic Resonance Imaging) apparatus, an ultrasonic diagnostic apparatus, etc.

A medical image capturing apparatus according to an embodiment includes image generation circuitry, detection circuitry, diagnosis support processing circuitry, setting circuitry, and imaging control circuitry. The image generation circuitry generates image data of a subject. The detection circuitry detects each of a plurality of parts of the subject in the image data generated as a positioning image. The diagnosis support processing circuitry executes diagnosis support processing corresponding to a predetermined part with regard to a region corresponding to the predetermined part of the subject detected by the detection circuitry in the image data. The setting circuitry sets an imaging condition of main imaging with respect to a part in which a lesion site is specified among the plurality of parts as a processing result of the diagnosis support processing circuitry. The imaging control circuitry controls an imaging mechanism to perform imaging with regard to an imaging region including the part in which the lesion site is specified based on the imaging condition.

First Embodiment

Figure 1:
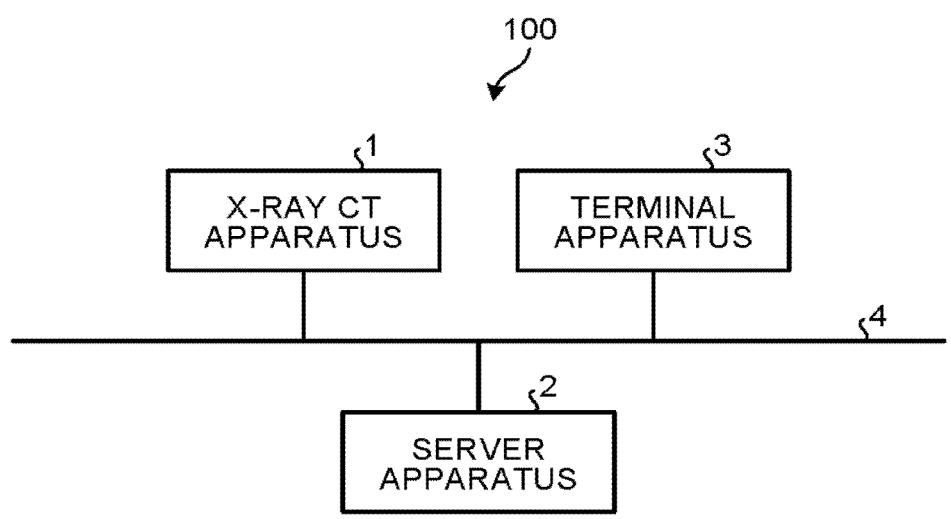
FIG. 1 is a diagram illustrating an example of a configuration of a medical information processing system according to a first embodiment.

FIG. 1 is a diagram illustrating an example of a configuration of the medical information processing system 100 according to the t embodiment. As illustrated in FIG. 1, the medical information processing system 100 according to the first embodiment includes an X-ray CT apparatus 1, a server apparatus 2, and a terminal apparatus 3. For example, the X-ray CT apparatus 1, the server apparatus 2, and the terminal apparatus 3 are in a state in which the apparatuses may directly or indirectly communicate with each other by a hospital LAN (Local Area Network) installed in a hospital. For example, when the PACS (Picture Archiving and Communication System) is introduced in the medical information processing system 100, the respective apparatuses mutually transmit and receive medical images, etc. according to a DICOM (Digital Imaging and Communications in Medicine) standard.

Further, in the medical information processing system 100, for example, a HIS (Hospital Information System), a RIS (Radiology Information System), etc. are introduced, and various types of information are managed. For example, the terminal apparatus 3 transmits an examination order created along the above-described system to the X-ray CT apparatus 1 or the server apparatus 2. The X-ray CT apparatus 1 acquires patient information from the examination order directly received from the terminal apparatus 3 or a patient list (modality work list) for each modality created by the server apparatus 2 receiving the examination order, and collects X-ray CT image data for each patient. Then, the X-ray CT apparatus 1 transmits the collected X-ray CT image data and image data generated by performing various types of image processing on the X-ray CT image data to the server apparatus 2. The server apparatus 2 stores the X-ray CT image data and the image data received from the X-ray CT apparatus 1, generates image data from the X-ray CT image data, and transmits image data corresponding to an acquisition request from the terminal apparatus 3 to the terminal apparatus 3. The terminal apparatus 3 displays the image data received from the server apparatus 2 on a monitor, etc. Each apparatus will be described below.

The terminal apparatus 3 is an apparatus that is disposed in each medical department of a hospital and operated by a doctor who works for each medical department, and corresponds to a PC (Personal Computer), a tablet PC, a FDA (Personal Digital Assistant), a mobile phone, etc. For example, medical record information such as a symptom of a patient or an opinion of a doctor is input to the terminal apparatus by the doctor. Further, the terminal apparatus receives an input of an examination order for ordering examination by the X-ray CT apparatus 1, and transmits the input examination order to the X-ray CT apparatus 1 and the server apparatus 2. That is, the doctor in the medical department manipulates the terminal apparatus 3, reads reception information and information of an electronic medical record of a visited patient, examines the corresponding patient, and inputs medical record information to the read electronic medical record. Then, the doctor in the medical department manipulates the terminal apparatus 3 and transmits the examination order according to the necessity of the examination by the X-ray CT apparatus 1.

The server apparatus 2 is an apparatus that stores a medical image (for example, X-ray CT image data and image data collected by the X-ray CT apparatus 1) collected by the medical image diagnostic apparatus or performs various types of image processing on the medical image. For example, the server apparatus 2 corresponds to a PACS server, etc. For example, the server apparatus 2 receives a plurality of examination orders from the terminal apparatus 3 disposed in each medical department, creates a patient list for each medical image diagnostic apparatus, and transmits the created patient list to each medical image diagnostic apparatus. As an example, the server apparatus 2 receives an examination order for performing an examination by the X-ray CT apparatus 1 from the terminal apparatus 3 of each medical department, creates a patient list, and transmits the created patient list to the X-ray CT apparatus 1. Then, the server apparatus 2 stores the X-ray CT image data and the image data collected by the X-ray CT apparatus 1 and transmits the X-ray CT image data and the image data to the terminal apparatus 3 according to the acquisition request from the terminal apparatus 3.

Figure 2:
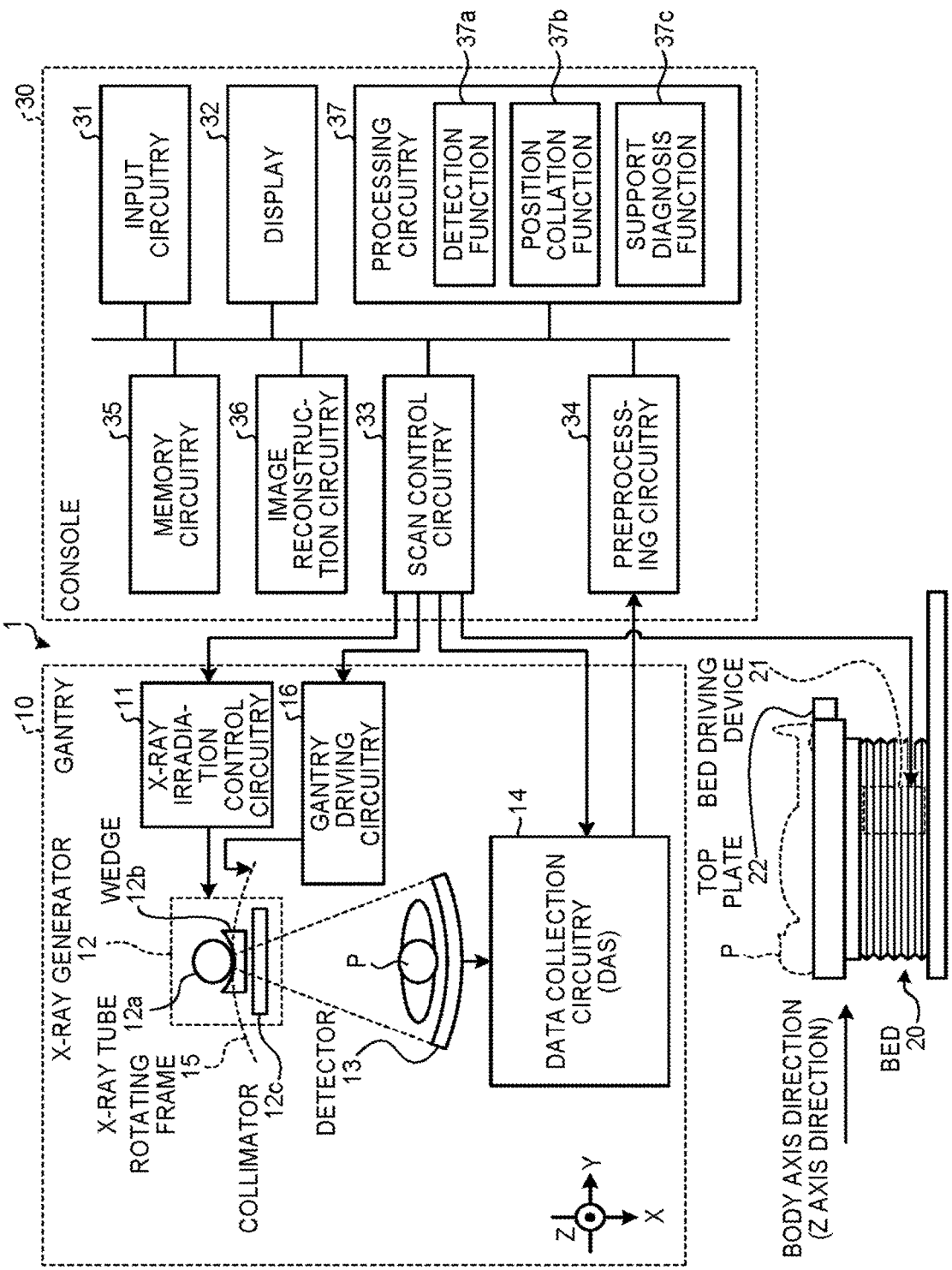
FIG. 2 is a diagram illustrating an example of a configuration of an X-ray CT apparatus according to the first embodiment.

The X-ray CT apparatus 1 collects X-ray CT image data for each patient, and transmits the collected X-ray CT image data or image data generated by performing various types of image processing on the X-ray CT image data to the server apparatus 2. FIG. 2 is a diagram illustrating an example of the configuration of the X-ray CT apparatus 1 according to the first embodiment. As illustrated in FIG. 2, the X-ray CT apparatus 1 according to the first embodiment includes a gantry 10, a bed 20, and a console 30.

The gantry 10 is a device that irradiates a subject P (patient) with an X-ray, detects an X-ray passing through the subject P, and outputs the X ray to the console 30, and includes X-ray irradiation control circuitry 11, an X-ray generator 12, a detector 13, data collection circuitry (DAS: Data Acquisition System) 14, a rotating frame 15, and gantry driving circuitry 16. The data collection circuitry 14 is an example of an acquisition circuitry.

The rotating frame 15 is an annular frame that supports the X-ray generator 12 and the detector 13 such that the X-ray generator 12 and the detector 13 face each other with the subject P interposed therebetween, and is rotated at a high speed in a circular orbit around the subject P by the gantry driving circuitry 16 described below.

The X-ray irradiation control circuitry 11 is a device that supplies a high voltage to an X-ray tube 12a as a high voltage generator, and the X-ray tube 12a generates an X-ray using the high voltage supplied from the X-ray irradiation control circuitry 11. The X-ray irradiation control circuitry 11 adjusts a dose of X-rays applied to the subject P by adjusting a tube voltage or a tube current supplied to the X-ray tube 12e under control of scan control circuitry 33 described below.

Further, the X-ray irradiation control circuitry 11 switches a wedge 12b. In addition, the X-ray irradiation control circuitry 11 adjusts an X-ray irradiation range (a fan angle and a cone angle) by adjusting an aperture of a collimator 12c. In the present embodiment, a plurality of types of wedges may be manually switched by an operator.

The X-ray generator 12 is a device for generating an X-ray and irradiating the subject P with the generated X-ray, and includes the X-ray tube 12a, the wedge 12b, and the collimator 12c.

The X-ray tube 12a is a vacuum tube that irradiates the subject P with an X-ray beam using a high voltage supplied by the high voltage generator (not illustrated), and irradiates the subject P with the X-ray beam in response to rotation of the rotating frame 15. The X-ray tube 12a generates an X-ray beam spreading with a fan angle and a cone angle. For example, under control of the X-ray irradiation control circuitry 11, the X-ray tube 12a may continuously emit an X-ray all around the subject P for full reconstruction, or continuously emit an X-ray at an irradiation range (130 degrees+fan angle) in which half reconstruction is allowed for half reconstruction. In addition, under control of the X-ray irradiation control circuitry 11, the X-ray tube 12a may intermittently emit an X-rays (pulse X-ray) at a preset position (tube position). In addition, the X-ray irradiation control circuitry 11 may modulate intensity of the X-ray emitted from the X-ray tube 12a. For example, the X-ray irradiation control circuitry 11 increases the intensity of the X-ray emitted from the X-ray tube 12a at a specific tube position, and decreases the intensity of the X-ray emitted from the X-ray tube 12a in a range other than the specific tube position.

The wedge 12b is an X-ray filter for adjusting the X-ray dose of X-rays emitted from the X-ray tube 12a. Specifically, the wedge 12b is a filter that transmits and attenuates an X-ray emitted from the X-ray tube 12a such that X-rays emitted from X-ray tube 12a to the subject P has a predetermined distribution. For example, the wedge 12b is a filter obtained by processing aluminum to have a predetermined target angle or a predetermined thickness. The wedge is also referred to as a wedge filter or a bow-tie filter.

The collimator 12c is a slit for narrowing the irradiation range of X-rays whose X-ray dose has been adjusted by the wedge 12b under control of the X-ray irradiation control circuitry 11 described below.

The gantry driving circuitry 16 turns the X-ray generator 12 and the detector 1 on a circular orbit around the subject P by rotating the rotating frame 15.

The detector 13 is a two-dimensional (2D) array type detector (surface detector) that detects an X-ray transmitting the subject P. Further, a plurality of detecting element rows, each of which is formed by arranging X-ray detecting elements corresponding to a plurality of channels, is arranged along a body axis direction axis direction illustrated in FIG. 2) of the subject P. Specifically, the detector 13 in the first embodiment has X-ray detecting elements arranged in a plurality of rows such as 320 rows along the body axis direction of the subject P. For example, the detector 13 may detect an X-ray passing through the subject P in a wide range such as a range including lungs and a heart of the subject P.

The data collection circuitry 14 is a DAS, and collects projection data from detection data of an X-ray detected by the detector 13. For example, the data collection circuitry 14 performs amplification processing, A/D conversion processing, sensitivity correction processing between channels, etc. on X-ray intensity distribution data detected by the detector 13 to generate projection data, and transmits the generated projection data to the console 30 described below. For example, when X-rays are continuously emitted from the X-ray tube 12a during rotation of the rotating frame 15, the data collection circuitry 14 collects a projection data group corresponding to a whole circumference (360 degrees). In addition, the data collection circuitry 14 associates each collected projection data with a tube position, and transmits the tube position associated with each collected projection data to the console 30 described below. The tube position is information indicating a projection direction of projection data. The sensitivity correction processing between channels may be performed by preprocessing circuitry 34 described below.

The bed 20 is a device for placing the subject P, and includes a bed driving device 21 and a top plate 22 as illustrated in FIG. 2. The bed driving device 21 moves the top plate 22 in the Z axis direction and moves the subject P into the rotating frame 15. The top plate 22 is a plate on which the subject P is placed.

For example, the gantry 10 executes helical scanning in which the subject P is scanned in a spiral shape by rotating the rotating frame 15 while moving the top plate 22. Alternatively, the gantry 10 executes conventional scanning in which the subject P is scanned in a circular orbit by rotating the rotating frame 15 while a position of the subject P is fixed after the top plate 22 is moved. Alternatively, the gantry 10 executes a step-and-shoot scheme of performing conventional scanning in a plurality of scan areas by moving a position of the top plate 22 at a certain interval.

The console 30 is a device that receives an operation of the X-ray CT apparatus by the operator and reconstructs the X-ray CT image data using the projection data collected by the gantry 10. As illustrated in FIG. 2, the console 30 includes input circuitry 31, a display 32, the scan control circuitry 33, the preprocessing circuitry 34, memory circuitry 35, image reconstruction circuitry 36, and processing circuitry 37. The scan control circuitry 33 is an example of imaging control circuitry, and the preprocessing circuitry 34 and the image reconstruction circuitry 36 are examples of acquisition circuitry.

The input circuitry 31 has a mouse, a keyboard, a trackball, a switch, a button, a joystick, etc. used by the operator of the X-ray CT apparatus 1 to input various instructions and various settings, and transmits information of the instructions and the settings received from the operator to the processing circuitry 37. For example, the input circuitry 31 receives an imaging condition of the X-ray CT image data, a reconstruction condition at the time of reconstructing the X-ray CT image data, an image processing condition for the X-ray CT image data, etc. from the operator. Further, the input circuitry 31 receives an operation for selecting an examination on the subject. Further, the input circuitry 31 receives a designation operation for designating a part on an image.

The display 32 is a monitor referred to by the operator. Under control of the processing circuitry 37, the display 32 displays image data generated from the X-ray CT image data to the operator, or displays a GUI (Graphical User Interface) for receiving various instructions, various settings, etc. from the operator through the input circuitry 31. Further, the display 32 displays a planning screen of a scan plan, a screen during scanning, etc. Further, the display 32 displays a virtual patient image including exposure information, image data, etc. The virtual patient image displayed by the display 32 will be described in detail below.

The scan control circuitry 33 controls a process of collecting projection data on the gantry 10 by controlling an imaging mechanism. Here, for example, the imaging mechanism includes the X-ray irradiation control circuitry 11, the gantry driving circuitry 16, the data collection circuitry 14, and the bed driving device 21. That is, the scan control circuitry 33 controls the process of collecting projection data on the gantry 10 by controlling operations of the X-ray irradiation control circuitry 11, the gantry driving circuitry 16, the data collection circuitry 14, and the bed driving device 21 under control of the processing circuitry 37. Specifically, the scan control circuitry 33 controls processes of collecting projection data in imaging of collecting a positioning image (scanogram image) and main imaging (scanning) of collecting an image used for diagnosis, respectively. Here, in the X-ray CT apparatus 1 according to the first embodiment, a 2D scanogram image and a 3D scanogram image may be captured.

For example, the scan control circuitry 33 fixes the X-ray tube 12a a 0° position (a position in a front direction with respect to the subject P), and captures a 2D scanogram image by continuously performing imaging while moving the top plate at a constant speed. Alternatively, the scan control circuitry 33 fixes the X-ray tube 12a at the 0° position, and captures a 2D scanogram image by continuously repeating imaging in synchronization with movement of the top plate while intermittently moving the top plate. Here, the scan control circuitry 33 may capture a positioning image not only in the front direction with respect to the subject but also in any direction (for example, in a lateral direction).

Figure 3:
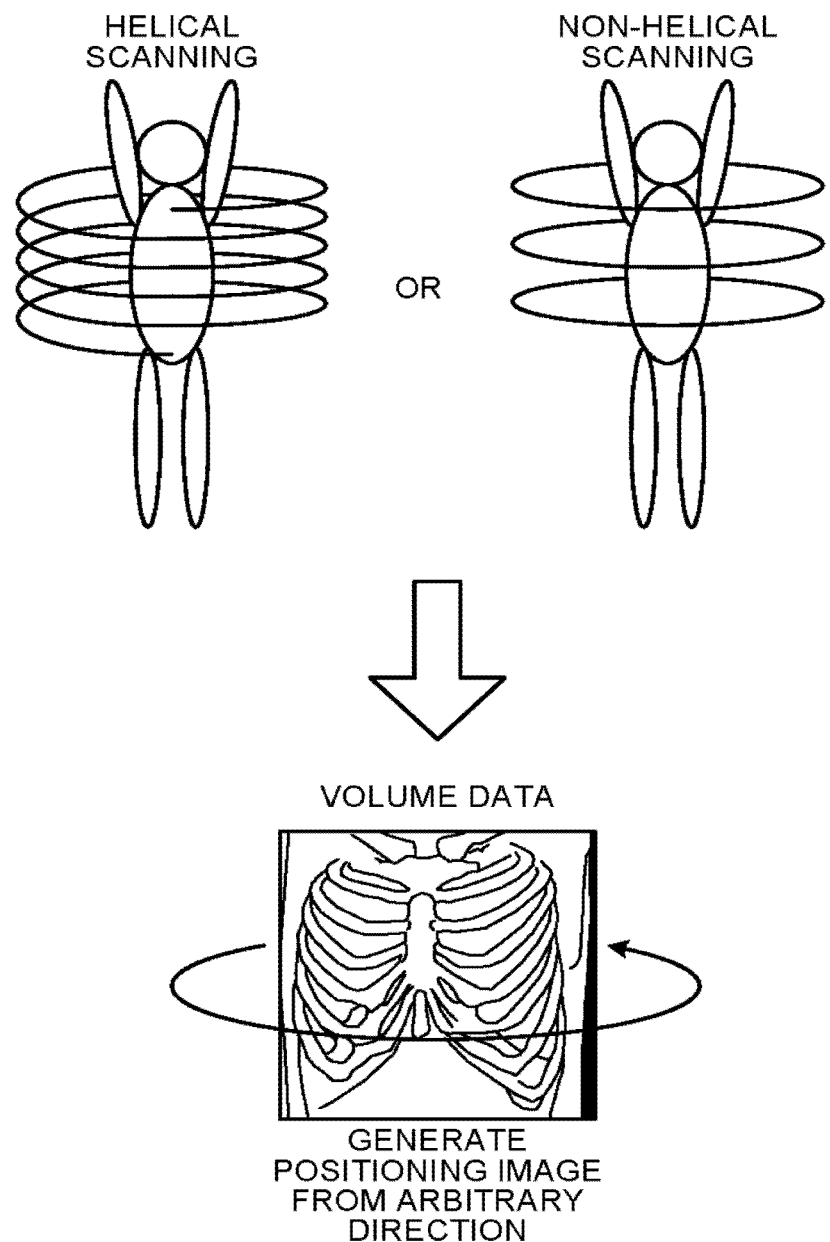
FIG. 3 is a diagram for description of three-dimensional (3D) scanogram imaging by scan control circuitry according to the first embodiment.

In addition, the scan control circuitry 33 captures a 3D scanogram image by collecting projection data for the whole circumference of the subject in capturing the scanogram image. FIG. 3 is a diagram for description of 3D scanogram imaging by the scan control circuitry 33 according to the first embodiment. For example, as illustrated in FIG. 3, the scan control circuitry 33 collects projection data for the whole circumference of the subject by helical scanning or non-helical scanning. Here, the scan control circuitry 33 executes helical scanning or non-helical scanning at a lower dose than the main imaging for a wide range such as a whole chest, a whole abdomen, a whole upper body, a whole body, etc. of the subject. As non-helical scanning, for example, the above-described step-and-shoot type scanning is executed.

As described above, when the scan control circuitry 33 collects the projection data for the whole circumference of the subject, the image reconstruction circuitry 36 described below may reconstruct 3D X-ray CT image data (volume data), and generate a positioning image from an arbitrary direction using the reconstructed volume data as illustrated in FIG. 3. Here, whether to capture the positioning image two-dimensionally or three-dimensionally may be arbitrarily set by the operator or set in advance according to inspection content.

Returning to FIG. 2, the preprocessing circuitry 34 performs correction processing such as logarithmic conversion processing, offset correction, sensitivity correction, and beam hardening correction on the projection data generated by the data collection circuitry 14, thereby generating corrected projection data. Specifically, the preprocessing circuitry 34 generates corrected projection data for each of the projection data of the positioning image generated by the data collection circuitry 14 and the projection data collected by the main imaging, and stores the corrected projection data in the memory circuitry 35.

The memory circuitry 35 stores the projection data generated by the preprocessing circuitry 34. Specifically, the memory circuitry 35 stores the projection data of the positioning image generated by the preprocessing circuitry 34 and the projection data for diagnosis collected by the main imaging. Further, the memory circuitry 35 stores image data generated by the image reconstruction circuitry 36 described below and a virtual patient image. Further, the memory circuitry 35 appropriately stores a processing result by the processing circuitry 37 to be described below. The virtual patient image and the processing result by the processing circuitry 37 will be described below.

The image reconstruction circuitry 36 reconstructs the X-ray CT image data by using the projection data stored in the memory circuitry 35. Specifically, the image reconstruction circuitry 36 reconstructs the X-ray CT image data from each of the projection data of the positioning image and the projection data of the image used for the diagnosis. Here, various schemes are present as a reconstruction scheme, and examples thereof include back projection processing. In addition, examples of the back projection processing include back projection processing by FBP (Filtered Back Projection). Alternatively, the image reconstruction circuitry 36 may reconstruct the X-ray CT image data using a successive approximation scheme.

In addition, the image reconstruction circuitry 36 generates image data by performing various types of image processing on the X-ray CT image data. Then, the image reconstruction circuitry 36 stores the reconstructed X-ray CT image data and the image data generated by the various types of image processing in the memory circuitry 35.

The processing circuitry 37 performs overall control of the X-ray CT apparatus 1 by controlling operations of the gantry 10, the bed 20, and the console 30. Specifically, the processing circuitry 37 controls the scan control circuitry 33 to control a CT scan performed on the gantry 10. Further, the processing circuitry 37 controls the image reconstruction circuitry 36 to control image reconstruction processing and image generation processing in the console 30. Further, the processing circuitry 37 performs a control operation such that various types of image data stored in the memory circuitry 35 are displayed on the display 2.

Further, as illustrated in FIG. 2, the processing circuitry 37 executes a detection function 37a, a position collation function 37b, and a support diagnosis function 37c. Here, for example, respective processing functions executed by the detection function 37a, the position collation function 37b, and the support diagnosis function 37c which are components of the processing circuitry 37 illustrated in FIG. 2 are stored in the memory circuitry 35 in the form of a program executable by a computer. The processing circuitry 37 is a processor that implements a function corresponding to each program by reading each program from the memory circuitry 35 and executing the read program. In other words, the processing circuitry 37 reading each program has each function illustrated in the processing circuitry 37 of FIG. 2. The detection function 37a is an example of detection circuitry, and the support diagnosis function 37c is an example of diagnosis support processing circuitry and setting circuitry.

The detection function 37a detects a plurality of parts in the subject P included in the 3D image data. Specifically, the detection function 37a detects a part of an organ, etc. included in the 3D X-ray CT image data (volume data) reconstructed by the image reconstruction circuitry 36. For example, the detection function 37a detects a part such as an organ based on an anatomical feature point (anatomical landmark) for at least one of volume data of the positioning image and volume data of the image used for diagnosis. Here, the anatomical feature point is a point indicating a feature of a part such as a specific bone, organ, blood vessel, nerve, lumen, etc. That is, the detection function 37a detects a bone, an organ, a blood vessel, a nerve, a lumen, etc. included in volume data by detecting an anatomical feature point of a specific organ, bone, etc. In addition, the detection function 37a may detect a position of a head, a neck, a chest, an abdomen, a leg, etc. included in volume data by detecting a characteristic feature point of a human body. A part described in the present embodiment refers to a bone, an organ, a blood vessel, a nerve, a lumen, etc. including a position thereof. Hereinafter, an example of detection of a part by the detection function 37a will be described. A "part detection processing" executed by the detection function 37a is also referred to as "AL analysis".

For example, the detection function 37a extracts an anatomical feature point from a voxel value included in volume data in the volume data of the positioning image or the volume data of the image used for diagnosis. Then, the detection function 37a compares a 3D position of the anatomical feature point in information such as a textbook with a position of the feature point extracted from the volume data to eliminate an inaccurate feature point from feature points extracted from the volume data, thereby optimizing the position of the feature point extracted from the volume data. In this way, the detection function 37a detects each part of the subject P included in the volume data. As an example, the detection function 37a first extracts an anatomical feature point included in the volume data using a supervised machine learning algorithm. Here, the supervised machine learning algorithm described above is constructed using a plurality of teacher images in which correct anatomical feature points are manually arranged. For example, a decision forest, etc. is used.

Then, the detection function 37a optimizes the extracted feature point by comparing a model indicating a 3D positional relationship of anatomical feature points in the body with the extracted feature point. Here, the above-described model is constructed using the above-described teacher image, and for example, a point distribution model, etc. is used. That is, the detection function 37a compares the extracted feature point with a model in which a shape or a positional relationship of the part, a point unique to the part, etc. are defined based on the plurality of teacher images in which correct anatomical feature points are manually arranged to eliminate an inaccurate feature point, thereby optimizing the feature point.

Figure 4A:
FIG. 4A is a diagram for description of an example of part detection processing by a detection function according to the first embodiment.
Figure 4B:
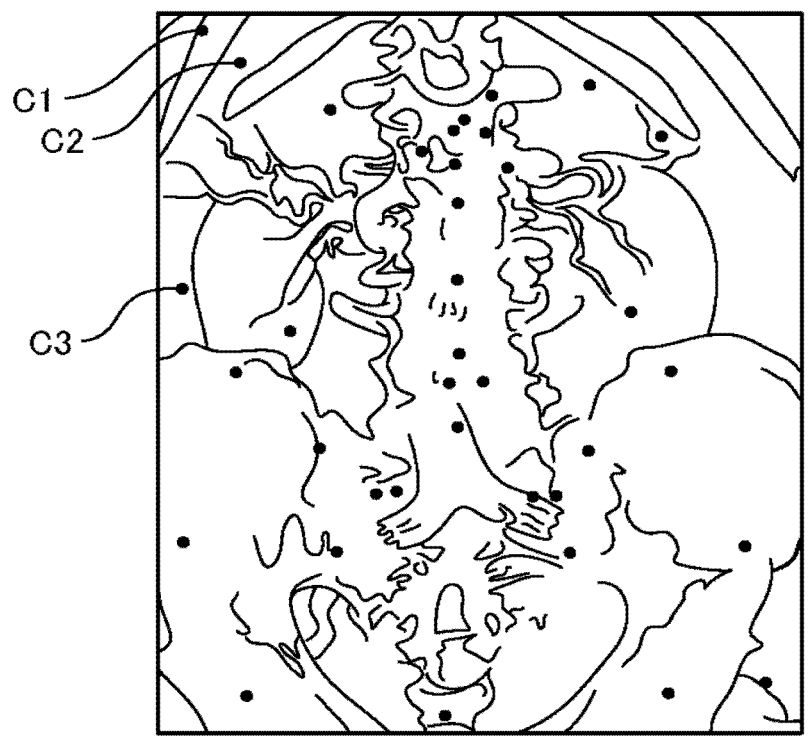
FIG. 4B is a diagram for description of an example of part detection processing by the detection function according to the first embodiment.

Hereinafter, an example of part detection processing by the detection function 37a will be described with reference to FIGS. 4A, 4B, 5, and 6. FIGS. 4A, 4B, 5, and 6 are diagrams for description of an example of part detection processing by the detection function 37a according to the first embodiment. In FIGS. 4A and 4B, feature points are arranged on two dimensions. However, in practice, feature points are three-dimensionally arranged. For example, the detection function 37a extracts voxels regarded as anatomical feature points (black dots in the figure) as illustrated in FIG. 4A by applying the supervised machine learning algorithm to the volume data. Then, the detection function 37a fits positions of the extracted voxels to a model in which a shape or a positional relationship of a part, a point unique to the part, etc. are defined to eliminate an inaccurate feature point among the extracted voxels, thereby extracting only voxels corresponding to more accurate feature points as illustrated in FIG. 4B.

Here, the detection function 37a assigns an identification code for identifying a feature point indicating a feature of each part to the extracted feature point (voxel), appends information, in which the identification code is associated with position (coordinate) information of each feature point, to image data, and stores the image data in the memory circuitry 35. For example, as illustrated in FIG. 4B, the detection function 37a assigns identification codes such as C1, C2, and C5 to extracted feature point (voxels). Here, the detection function 37a appends an identification code to each data subjected to detection processing, and stores the data in the memory circuitry 35. Specifically, the detection function 37a detects a part of the subject included in volume data reconstructed from at least one of projection data of a positioning image, projection data collected under non-contrast, and projection data collected in a state contrast-enhanced by a contrast agent.

For example, as illustrated in FIG. 5, the detection function 37a appends information, in which an identification code is associated with coordinates of each voxel detected from the volume data (positioning in the figure) of the positioning image, to volume data, and stores the volume data in the memory circuitry 35. As an example, the detection function 37a extracts coordinates of a marker point from the volume data of the positioning image, and stores the coordinates by associating the coordinates with volume data such as "identification code: C1, coordinates $(x_1, y_1, z_1)$", "identification code: C2, coordinates $(x_2, y_2, z_2)$", etc. as illustrated in FIG. 5. In this way, the detection function 37a may identify a type of position and a type of feature point in the volume data of the positioning image, and detect each part of an organ, etc. based on these pieces of information.

Further, for example, as illustrated in FIG. 5, the detection function 37a appends information in which an identification code is associated with coordinates of each voxel detected from volume data (scan in the figure) of a diagnostic image, to the volume data, and stores the volume data in the memory circuitry 35. Here, in scanning, the detection function 37a may extract coordinates of a marker point from each of volume data (contrast Phase in the drawing) contrast-enhanced by the contrast agent and volume data (non-contrast Phase in the figure) not contrasted by the contrast agent, and associate an identification code with the extracted coordinates.

As an example, the detection function 37a extracts the coordinates of the marker point from the volume data of the non-contrast Phase in the volume data of the diagnostic image, and stores the coordinates by associating the coordinates with volume data such as "identification code: C1, coordinates $(x'_1, y'_1, z'_1)$", "identification code: C2, coordinates $(x'_2, y'_2, z'_2)$", etc. as illustrated in FIG. 5. In addition, the detection function 37a extracts the coordinates of the marker point from the volume data of the contrast Phase in the volume data of the diagnostic image, and stores the coordinates by associating the coordinates with volume data such as "identification code: C1, coordinates $(x'_1, y'_1, z'_1)$", "identification code: C2, coordinates $(x'_2, y'_2, z'_2)$", etc. as illustrated in FIG. 5. Here, in the case of extracting a marker point from the volume data of the contrast Phase, a marker point which can be extracted by being contrasted is included. For example, when a marker point is extracted from the volume data of the contrast Phase, the detection function 37a may extract a blood vessel, etc. contrasted by the contrast agent. Therefore, in the case of the volume data of the contrast Phase, as illustrated in FIG. 5, the detection function 37a associates identification codes C31, C32, C33, and C34 for identifying respective blood vessels with coordinates $(x'_{31}, y'_{31}, z'_{31})$ to coordinates $(x'_{34}, y'_{34}, z'_{34})$ of marker points of blood vessels extracted by being contrasted.

As described above, the detection function 37a may identify a type of position and a type of marker point in the volume data of the positioning image or the diagnostic image, and detect each part of an organ, etc. based on these pieces of information. For example, the detection function 37a detects a position of a target part to be detected using information about an anatomical positional relationship between the target part and a part around the target part. As an example, when the target part is a "lung", the detection function 37a acquires coordinate information associated with an identification code indicating a characteristic of the lung, and acquires coordinate information associated with an identification code indicating a part around the "lung" such as a "rib", a "clavicle", "heart", a "diaphragm", etc. Then, the detection function 37a extracts a region of the "lung" in the volume data using information about an anatomical positional relationship between the "lung" and the part around the "lung" and the acquired coordinate information.

Figure 6:
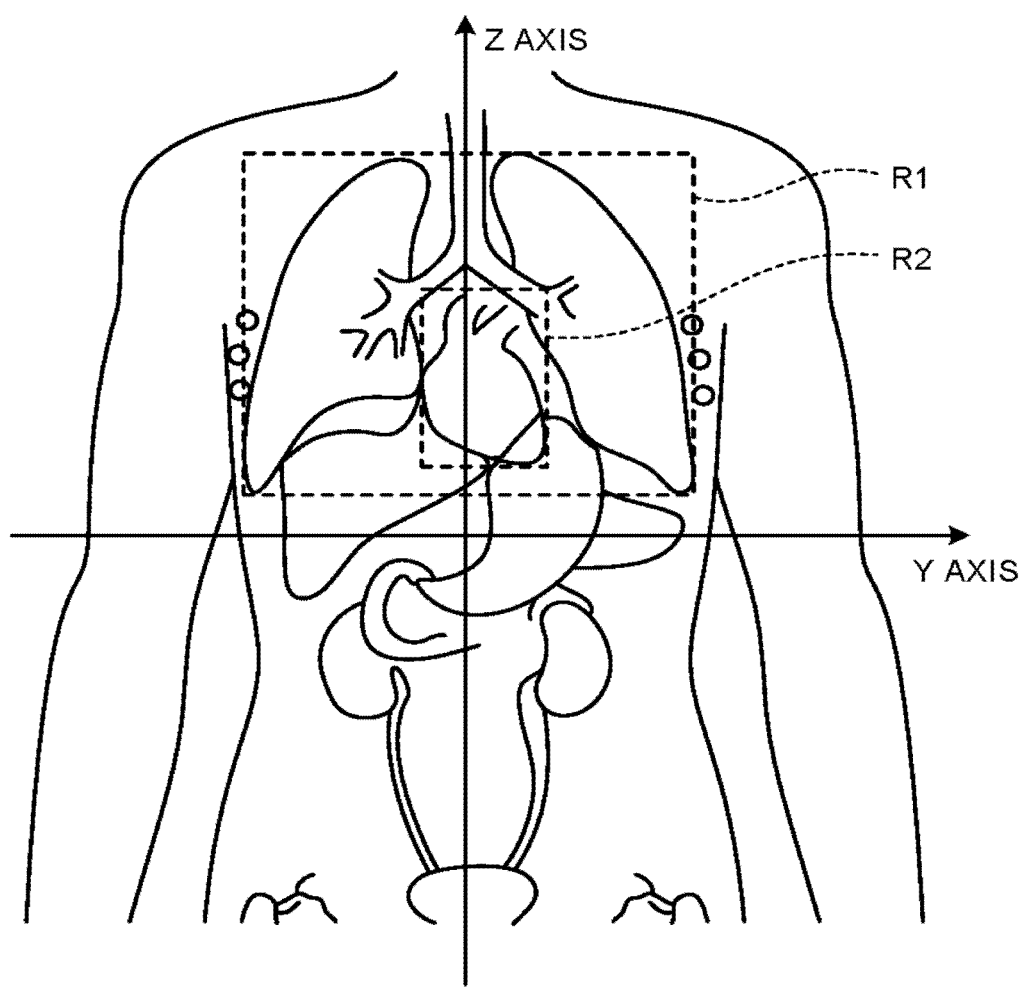
FIG. 6 is a diagram for description of an example of part detection processing by the detection function according to the first embodiment.

For example, as illustrated in FIG. 6, the detection function 37a extracts a region R1 corresponding to the "lung" in the volume data from information about a positional relationship such as "an apex of the lung: 2 to 3 cm above the clavicle", "a lower end of the lung: a height of a seventh rib", etc. and coordinate information of each part. That is, the detection function 37a extracts coordinate information of a voxel of the region R1 in the volume data. The detection function 37a associates the extracted coordinate information with part information, appends the information to the volume data, and stores the volume data in the memory circuitry 35. Similarly, as illustrated in FIG. 6, the detection function 37a may extract a region R2 corresponding to the "heart" in the volume data.

Further, the detection function 37a detects a position included in the volume data based on feature points defining positions of a head, a chest, etc. in the human body. Here, the positions of the head, the chest, etc. in the human body may be arbitrarily defined. For example, when an area from a seventh cervical vertebra to a lower end of the lung is defined as the chest, the detection function 37a detects a feature point corresponding to the seventh cervical vertebra to a feature point corresponding to the lower end of the lung as the chest. In addition to a scheme using the above-described anatomical feature point, the detection function 37a may detect a part using various schemes. For example, the detection function 37a may detect a part included in volume data using a region expansion scheme based on a voxel value.

The position collation function 37b collates a position of each of a plurality of parts in the subject included in the 3D image data with a position of each of a plurality of parts in the human body included in virtual patient data. Here, the virtual patient data is information representing a standard position of each of the plurality of parts in the human body. That is, the position collation function 37b collates a part of the subject with a position of the standard part, and stores a collation result in the memory circuitry 35. For example, the position collation function 37b matches a virtual patient image in which the part of the human body is disposed at the standard position with volume data of the subject.

Here, first, the virtual patient image will be described. The virtual patient image is generated in advance as an image actually captured by an X-ray with regard to a human body having a standard physique according to a plurality of combinations of parameters related to physiques such as age, adult/child, male/female, weight, height, etc., and is stored the memory circuitry 35. That is, the memory circuitry 35 stores data of a plurality of virtual patient images according to the above-described combinations of parameters. Here, an anatomical feature point (feature point) is stored in association with the virtual patient image stored by the memory circuitry 35. For example, the human body has numerous anatomical feature points which can be extracted from an image relatively easily by image processing such as pattern recognition based on morphological features thereof, etc. Locations and arrangement of these numerous anatomical feature points in the body are roughly determined according to physiques such as age, adult/child, male/female, weight, height, etc.

Figure 7:
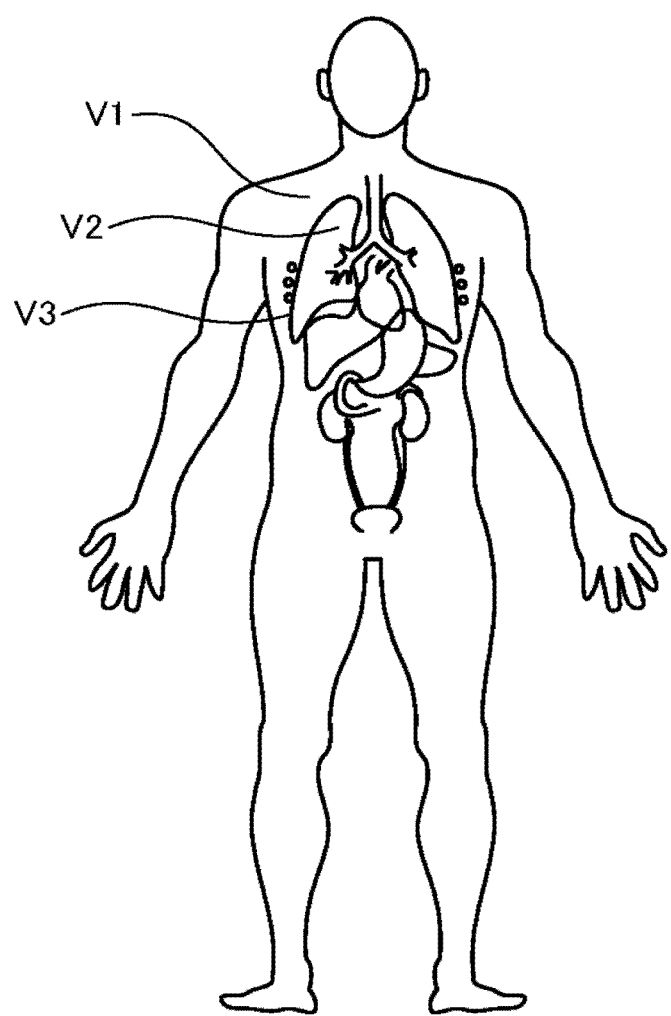
FIG. 7 is a diagram illustrating an example of a virtual patient image stored by memory circuitry according to the first embodiment.

These numerous anatomical feature points of the virtual patient image stored by the memory circuitry 35 are detected in advance, and position data of the detected feature points is stored by being appended to or associated with data of the virtual patient image together with identification codes of the respective feature points. FIG. 7 is a diagram illustrating an example of the virtual patient image stored by the memory circuitry 35 according to the first embodiment. For example, as illustrated in FIG. 7, the memory circuitry 35 stores a virtual patient image in which anatomical feature points are associated with identification codes "V1", "V2", and "V3" for identifying the feature points in a 3D human body including a part such as an organ.

That is, the memory circuitry 35 associates and stores coordinates of a feature point in a coordinate space of a 3D human body image with an identification code corresponding thereto. As an example, the memory circuitry 35 stores coordinates of a corresponding feature point in association with the identification code "V1" illustrated in FIG. 7. Similarly, the memory circuitry 35 stores the identification code and the coordinates of the feature point associated with each other. FIG. 7 only illustrates a lung, a heart, a liver, a stomach, a kidney, etc. as organs. However, in practice, the virtual patient image further includes numerous organs, bones, blood vessels, nerves, etc. Further, FIG. 7 only illustrates the feature points corresponding to the identification code "V1", "V2", and "V3". However, in practice, more numerous feature points are included.

Figure 8:
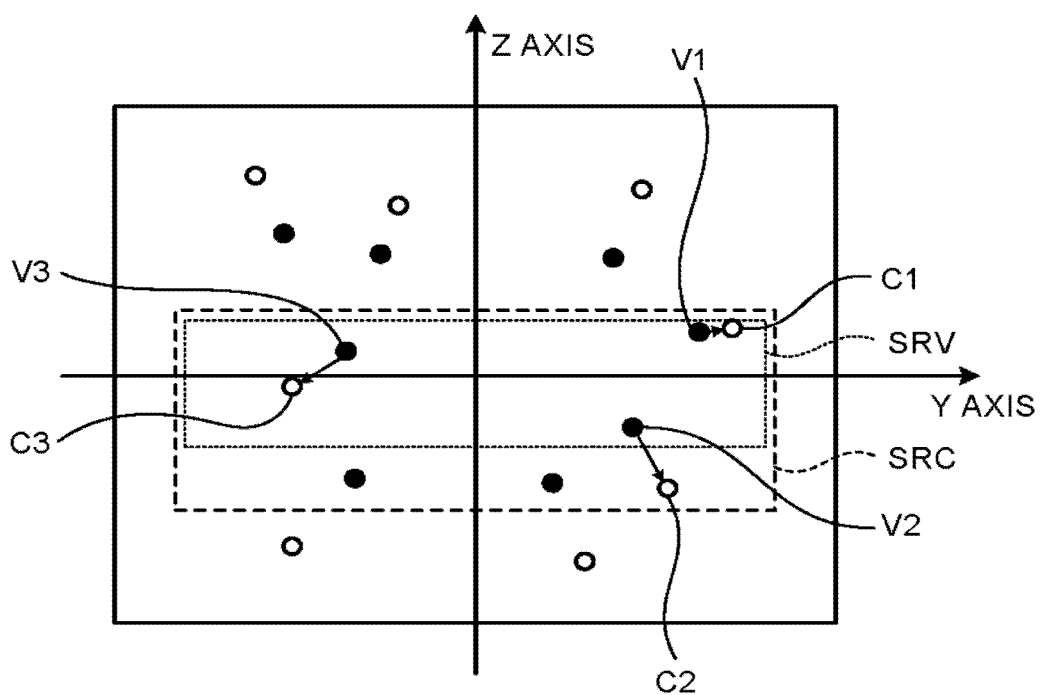
FIG. 8 is a diagram for description of an example of collation processing by a position collation function according to the first embodiment.

The position collation function 37b matches a feature point in the volume data of the subject detected by the detection function 37a with a feature point in the above-described virtual patient image using an identification code, and associates a coordinate space of the volume data with a coordinate space of the virtual patient image. FIG. 8 is a diagram for description of an example of collation processing by the position collation function 37b according to the first embodiment. Here, FIG. 8 illustrates a case in which matching is performed using three sets of feature points to which an identification code indicating the same feature point is assigned between a feature point detected from the scanogram image and a feature point detected from the virtual patient image. However, the embodiment is not limited thereto, and matching may be performed using an arbitrary set of feature points.

For example, as illustrated in FIG. 8, when feature points indicated by the identification codes "V1", "V2", and "V3" in the virtual patient image are matched with feature points indicated by the identification codes "C1", "C2", and "C3" in the scanogram image, the position collation function 37b performs coordinate transformation such that positional deviation between the same feature points is minimized, thereby associating coordinate spaces between the images. For example, as illustrated in FIG. 8, the position collation function 37b obtains a coordinate transformation matrix "H" below to minimize a sum "LS" of positional deviations between the same anatomical feature points "V1(x1, y1, z1), C1(X1, Y1, Z1)", "V2(x2, y2, z2), C2(X2, Y2, Z2)", and "V3(x3, y3, C3(X3, Y3, Z3)".

$$LS = ((X1, Y1, Z1) \cdot H(x1, y1, z1)) +$$
$$((X2, Y2, Z2) \cdot H(x2, y2, z2)) + ((X3, Y3, Z3) \cdot H(x3, y3, z3))$$

Figure 9:
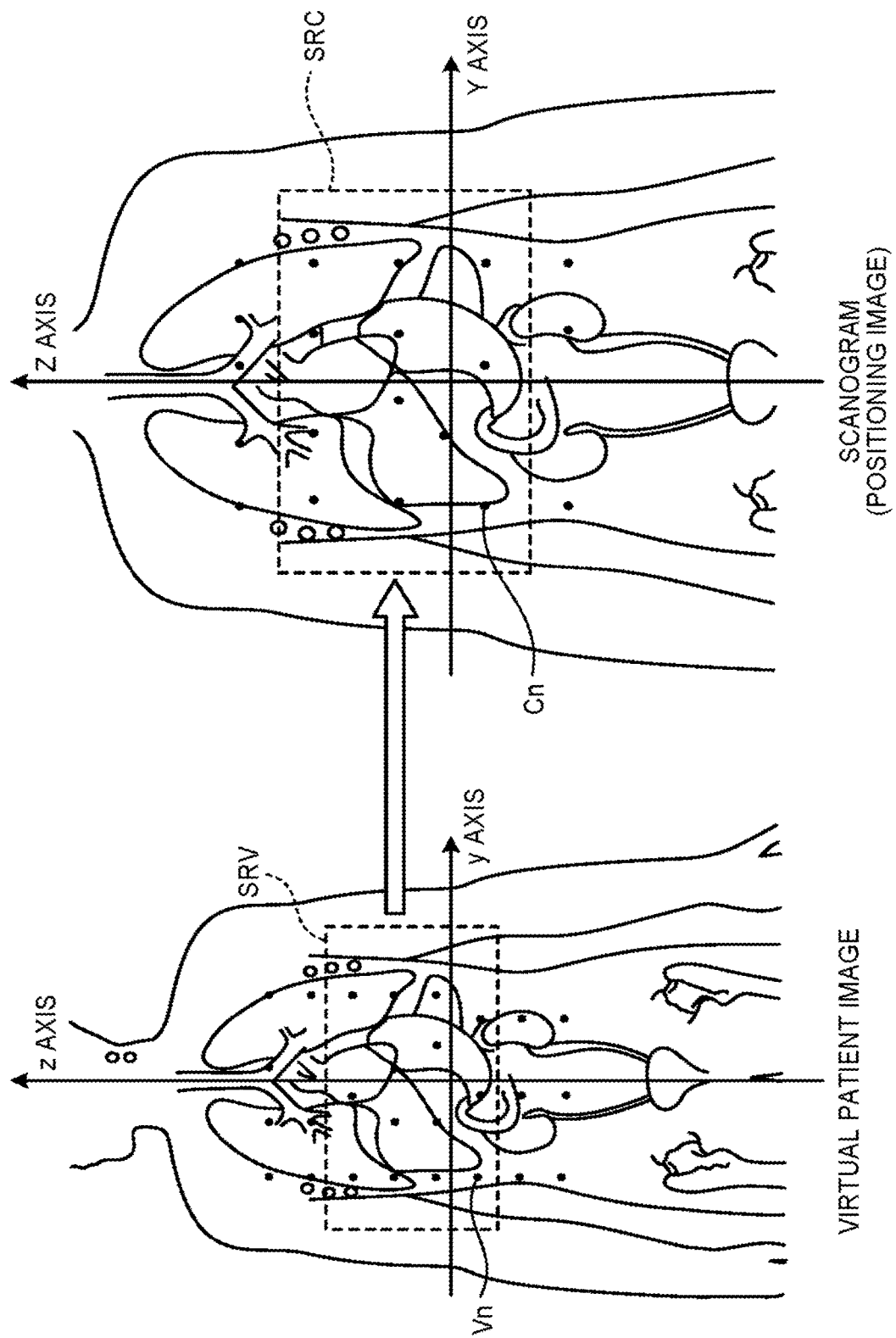
FIG. 9 is a diagram showing an example of conversion of a scan range by coordinate transformation according to the first embodiment.

The position collation function 37b may convert a scan range designated on the virtual patient image into a scan range on the positioning image by the obtained coordinate transformation matrix "H". For example, as illustrated in FIG. 8, the position collation function 37b may convert a scan range "SRV" designated on the virtual patient image into a scan range "SRC" on the positioning image using the coordinate transformation matrix "H". FIG. 9 is a diagram illustrating an example of conversion of a scan range using coordinate transformation according to the first embodiment. For example, when the operator sets a scan range "SRV" on a virtual patient image as illustrated on a virtual patient image of FIG. 9, the position collation function 37b converts the set scan range "SRV" into a scan range "SRC" on a scanogram image using the above-described coordinate transformation matrix "H".

In this way, for example, the scan range "SRV" set to include a feature point corresponding to an identification code "Vn" on the virtual patient image is set by being converted into the scan range "SRC" including an identification code "Cn" corresponding to the same feature point on the scanogram image. The above-described coordinate transformation matrix "H" may be stored in the memory circuitry 35 for each subject and appropriately read and used, or may be calculated each time a scanogram image is collected. As described above, according to the first embodiment, when a virtual patient image is displayed to designate a range at the time of presetting, and a position/range is planned thereon, a position/range on a positioning image corresponding to the planned position/range may be automatically set as a numerical value after the positioning image (scanogram image) is captured.

Returning to FIG. 2, the support diagnosis function 37c executes a computer aided diagnosis (CAD) process of detecting a lesion site on a reconstructed image of the subject using a predetermined support diagnosis algorithm. The support diagnosis function 37c will be described in detail below. In addition, the CAD is also referred to as diagnosis support processing.

The overall configuration of the medical information processing system 100 and the configuration of the X-ray CT apparatus 1 according to the first embodiment have been described above. Under the above-described configuration, the X-ray CT apparatus 1 according to the first embodiment improves accuracy of presetting of an image capturing position by converting a designated scan position or scan range based on a result of collating an anatomical feature point in a virtual patient image with a feature point based on a structure in the subject in image data captured by positioning scanning or main scanning.

Incidentally, in the X-ray CT apparatus 1, CAD (computer aided diagnosis) for detecting a lesion site may be executed on a reconstructed image of the subject using a predetermined support diagnosis algorithm in some cases. Here, in an X-ray CT apparatus according to a conventional technology, CAD has been performed on a reconstructed image obtained by main scanning.

In this case, for example, the radiologist performs CAD on the reconstructed image after an examination ends. Then, the radiologist interprets the reconstructed image with reference to a processing result of CAD. That is, in the X-ray CT apparatus according to the conventional technology, CAD could not be executed before main scanning in the same examination. In other words, an imaging condition of main scanning could not be optimized with reference to the processing result of CAD. As a result, even when the radiologist detects a lesion site and determines that a detailed examination is necessary, a patient has already returned home and a time until a reexamination becomes longer, or the patient is forced to have a plurality of examinations to increase a burden on the patient in some cases.

In view of the above description, the X-ray CT apparatus 1 according to the first embodiment executes support diagnosis processing for a part with respect to a positioning image for each of a plurality of the detected parts of the subject. Such a function is implemented by the support diagnosis function 37c. Hereinafter, the support diagnosis function 37c will be described.

Figure 10:
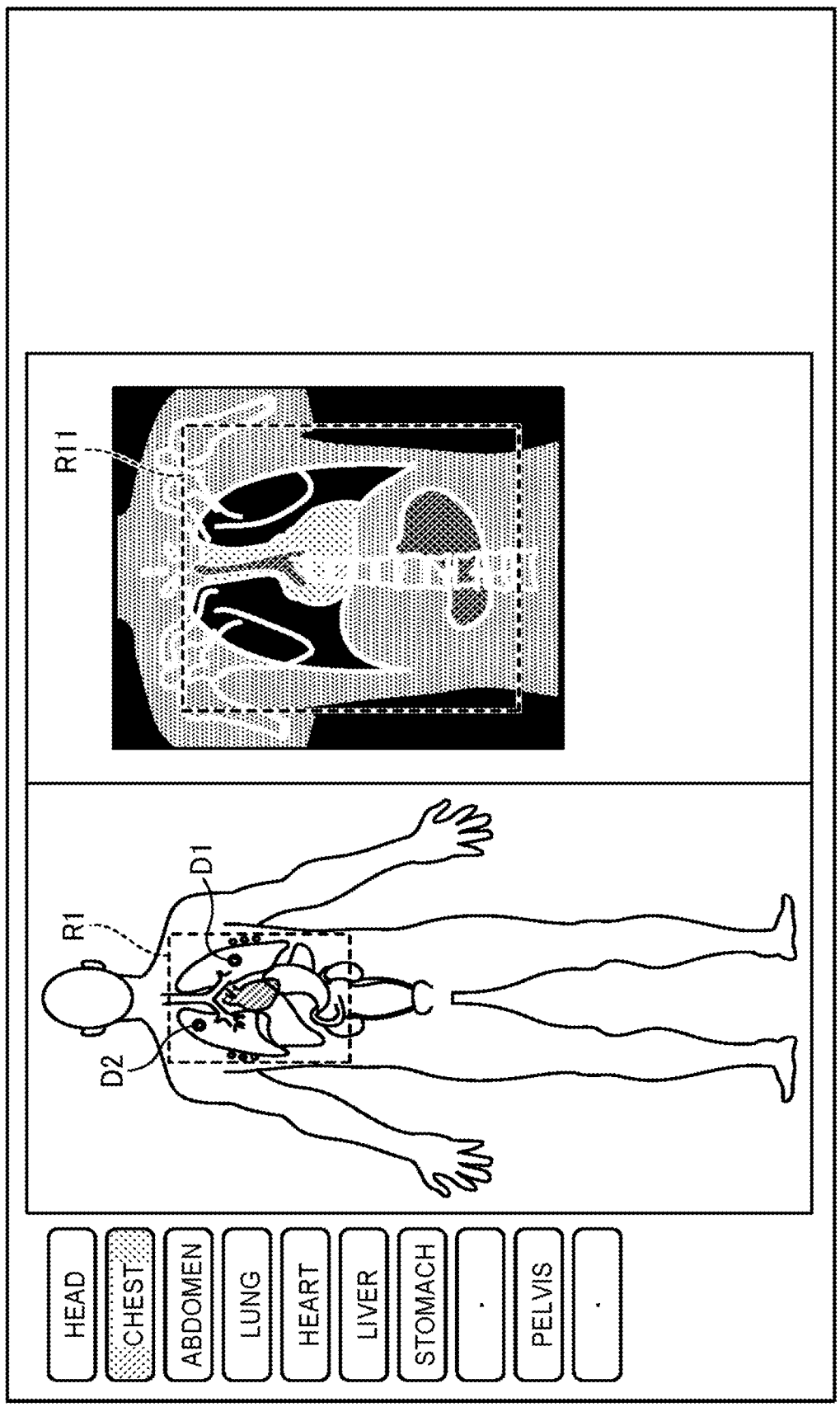
FIG. 10 is a diagram (1) for description of the first embodiment.

With regard to a region corresponding to a predetermined part of the subject detected by the detection function 37a in a positioning image, the support diagnosis function 37c executes diagnosis support processing corresponding to the predetermined part. For example, the support diagnosis function 37c detects a site having a possibility of disease using a predetermined support diagnosis algorithm for each part. More specifically, for example, when the part is the lung, the support diagnosis function 37c detects a tumor shadow or a shadow as a lesion site using a support diagnosis algorithm for lung cancer. Then, the support diagnosis function 37c displays a processing result on the display 32. Here, the support diagnosis function 37c causes the display 32 to display a result of diagnosis support processing on a virtual patient associated with each part of the subject. FIG. 10 is a diagram (1) for description of the first embodiment.

FIG. 10 illustrates a GUI screen when a positioning image is captured after a chest is set as a target part in presetting of main scanning. As illustrated in FIG. 10, buttons (for example, buttons of head, chest, abdomen, lung, heart, etc.) for designating a target part at the left end, a virtual patient image showing the whole human body, and a positioning image acquired by positioning scanning are displayed on the GUI screen. Further, as illustrated in FIG. 10, a processing result of diagnosis support processing is displayed on the virtual patient image. FIG. 10 illustrates a case in which a scan range R1 of the chest is set on the virtual patient image. When the scan range R1 is set on the virtual patient image, the position collation function 37b sets a scan range R11 through conversion into coordinate information on the positioning image.

Figure 12:
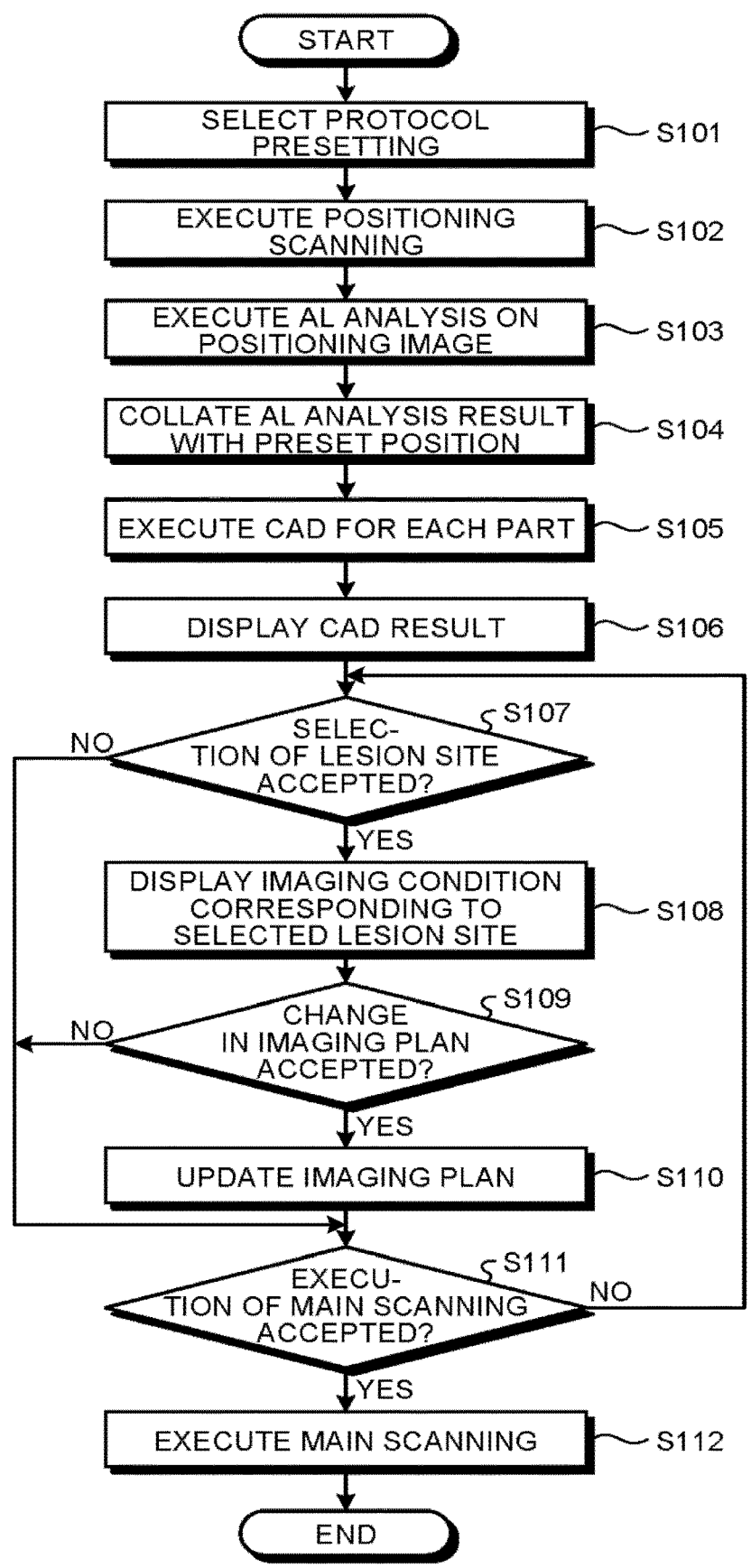
FIG. 12 is a flowchart illustrating a processing procedure by the X-ray CT apparatus according to the first embodiment.

FIG. 10 illustrates a case in which a lesion site D1 and a lesion site D2 are detected in the lung as a result of applying diagnosis support processing to a reconstructed image obtained by positioning scanning. Here, the support diagnosis function 37c corrects a display position of the result of diagnosis support processing according to a ratio between a positioning image and a virtual patient, and displays the result on the display. FIG. 12 illustrates a case in which the lesion site D1 and the lesion site D2 are displayed in the same form. However, the embodiment is not limited thereto. For example, the support diagnosis function 37c may display a processing result on the display 32 in a display form corresponding to importance. More specifically, a description will be given of a case in which importance is set based on a shape or a size of a tumor shadow or a shadow. Further, as importance increases, a possibility that a lesion site corresponds to a disease increases. For example, the support diagnosis function 37c may display a lesion site having high importance in a flickering manner, or display a lesion site having low importance and a lesion site having high importance in different colors.

When the processing result of diagnosis support processing is displayed on the virtual patient in this a the operator may confirm the lesion site with reference to the processing result of diagnosis support processing before main scanning. Here, the support diagnosis function 37c may assign information indicating whether the lesion site is confirmed by the operator. For example, the support diagnosis function 37c further displays a check box around the lesion site. Then, when the lesion site is confirmed, the support diagnosis function c accepts an input from the operator to the check box. Alternatively, the support diagnosis function 37c may convert a color of a lesion site indicated by the operator to indicate that the lesion site has been checked. In this way, the operator may distinguish a confirmed lesion site from an unconfirmed lesion site.

In addition, the operator may determine that it is desirable to change to imaging under a high-definition imaging condition or to add a high-definition imaging condition to a lesion site by referring to the processing result of diagnosis support processing. For this reason, the support diagnosis function 37c sets an imaging condition of main imaging with respect to a part in which a lesion site is specified among a plurality of parts as the processing result of diagnosis support processing. For example, the support diagnosis function 37c sets an imaging condition of main scanning with respect to a part in which a lesion site selected by the operator is specified among lesion sites specified as a result of diagnosis support processing.

More specifically, the support diagnosis function 37c sets a condition for executing high-definition imaging as an imaging condition. For example, when a selection of the lesion site D1 illustrated in FIG. 10 is accepted from the operator, the support diagnosis function 37c extracts a condition for executing high-definition imaging as an imaging condition with respect to the lesion site D1, and displays a pop-up window including this imaging condition on the display 32. FIG. 11 is a diagram (2) for description of the first embodiment. An example illustrated in FIG. 11 illustrates a case in which "collection thickness", "D-FOV", "kV", "C-FOV", "imaging range", and "reconstruction condition" are included as items of an imaging condition for executing high-definition imaging.

Here, the imaging condition illustrated in FIG. 11 includes a part preset by the operator and a part set by the support diagnosis function 37c based on a body shape, etc. As an example, the operator presets the collection thickness (for example, 0.25 mm, etc.) and the D-FOV in advance. Meanwhile, the support diagnosis function 37c calculates kV, mA, and C-FOV from an imaging condition of positioning scanning as a condition for executing high-definition imaging. In addition, the support diagnosis function 37c calculates a reconstruction condition (interval) from D-FOV to obtain an isotropic Voxel. Incidentally, an FHP method or a successive approximation reconstruction method is included as the reconstruction condition.

Further, as illustrated in FIG. 11, the support diagnosis function 37c displays "set" and "cancel". Here, when "cancel" is selected by the operator, the support diagnosis function 37c closes the pop-up window. That is, the operator may execute main scanning by ignoring a processing result of the CAD. On the other hand, when "set" is selected by the operator, the support diagnosis function 37c adds the imaging condition displayed in the pop-up window to an imaging plan.

It is possible to set an imaging condition which is set by the user or automatically calculated. For example, the support diagnosis function 37c may set at least one of a tube voltage, a tube current, an imaging range, and a reconstruction condition as a condition for executing high-definition imaging. In this way, for example, the support diagnosis function 37c extracts a condition for executing high-definition imaging as an imaging condition of main scanning with respect to a part in which a lesion site selected by the operator is specified.

In addition, when the imaging condition of the lesion site is not added, the scan control circuitry 33 executes main scanning under an imaging condition selected in advance as an imaging plan of main scanning. Further, when the imaging condition of the lesion site is added, the scan control circuitry 33 executes main scanning under the imaging condition selected in advance as the imaging plan of main scanning and the extracted imaging condition. That is, when the imaging condition of the lesion site is added, the scan control circuitry 33 controls the imaging mechanism so as to perform imaging with regard to an imaging region including a part in which the lesion site is specified based on the set imaging condition.

FIG. 12 is a flowchart illustrating a processing procedure by the X-ray CT apparatus 1 according to the first embodiment. FIG. 12 illustrates a flowchart for description of an operation of the entire X-ray CT apparatus 1, and describes which step of the flowchart each component corresponds to.

Step S101 is a step implemented by the input circuitry 31. In step S101, the input circuitry 31 accepts a selection of protocol presetting. Step S102 is a step implemented by the scan control circuitry 33. In step S102, the scan control circuitry 33 executes positioning scanning.

Step S103 is a step corresponding to the detection function 37a and is a step in which the detection function 37a is implemented when the processing circuitry 37 calls a predetermined program corresponding to the detection function 37a from the memory circuitry 35 and executes the program. In step S103, the detection function 37a executes AL analysis on a positioning image.

Step S104 is a step corresponding to the position collation function 37b and is a step in which the position collation function 37b is implemented when the processing circuitry 37 calls a predetermined program corresponding to the position collation function 37b from the memory circuitry 35 and executes the program. In step S104, the position collation function 37b collates an AL analysis result with a preset position.

Steps S105 to S110 are steps corresponding to the support diagnosis function 37c and are steps in which the support diagnosis function 37c is implemented when the processing circuitry 37 calls a predetermined program corresponding to the support diagnosis function 37c from the memory circuitry 35 and executes the program. In step S105, the support diagnosis function 37c executes CAD for each part. In step S106, the support diagnosis function 37c displays a result of CAD for each part.

In step S107, the support diagnosis function 37c determines whether a selection of a lesion site has been accepted. Here, when it is determined that the selection of the lesion site has not been accepted (step S107, No), the support diagnosis function 37c proceeds to step S111. On the other hand, when it is determined that the selection of the lesion site has been accepted (step S107, Yes), the support diagnosis function 37c displays an imaging condition corresponding to the selected lesion site in step S108.

Then, in step S109, the support diagnosis function 37c determines whether a change in imaging plan has been accepted. Here, when it is determined that the change in imaging plan has not been accepted (step S109, No), the support diagnosis function 37c proceeds to step S111. On the other hand, when it is determined that the change in imaging plan has been accepted (step S109, Yes), the support diagnosis function 37c updates the imaging plan in step S110. For example, the support diagnosis function 37c updates the imaging plan to execute an imaging condition for executing high-definition imaging in addition to an imaging condition selected in advance as an imaging plan of main scanning.

Step S111 is a step implemented by the scan control circuitry 33. In step S111, the scan control circuitry 33 determines whether execution of main scanning has been accepted. Here, when it is determined that execution of main scanning has not been accepted (step S111, No), the scan control circuitry 33 proceeds to step S107. On the other hand, when it is determined that execution of main scanning has been accepted (step S111, Yes), the scan control circuitry 33 executes main scanning in step S112.

The support diagnosis function 37c may perform diagnosis support processing on a 3D image generated by reconstructing projection data collected by main scanning, and display a processing result on the display 32. In such a case, the image reconstruction circuitry 36 generates 3D image data by reconstructing the projection data collected by main scanning. In addition, the detection function 37a detects a plurality of parts of the subject in the 3D image data. Then, the support diagnosis function 37c executes diagnosis support processing corresponding to a predetermined part with regard to a region corresponding to the predetermined part of the subject detected by the detection function 37a in the 3D image data acquired by main scanning. In this way, it possible to more accurately detect the lesion site by executing diagnosis support processing on a 3D image captured with high definition through main scanning. Further, in such a case, for example, the support diagnosis function 37c executes diagnosis support processing using a discrimination algorithm. In this way, a new lesion site may be detected.

As described above, in the first embodiment, prior to main scanning, support diagnosis processing for a corresponding part is executed on a positioning image for each of a plurality of the detected parts of a subject. In this way, the operator may easily find a part failing to be recognized as a part having a possibility of being a lesion site before main scanning. Further, an imaging condition of main scanning may be optimized with reference to a processing result of support diagnosis. For example, a condition for executing high-definition imaging on a lesion site is set. In this way, main scanning may be executed with an optimal does for a required location, at a fine slice thickness, and with a parameter overlapping a pitch. In this way, according to the first embodiment, it is possible to efficiently improve an image quality. As a result, according to the first embodiment, accurate interpretation of radiogram can be supported.

In addition, as a result, according to the first embodiment, for example, the radiologist may shorten time to perform an accurate diagnosis. Further, according to the first embodiment, it is possible to reduce the burden on the patient without forcing the patient to have a plurality of examinations.

In addition, in the first embodiment described above, a description has been given of a case in which the support diagnosis function 37c adds the imaging condition for executing high-definition imaging to the imaging condition selected in advance as the imaging plan of main scanning. However, the embodiment is not limited thereto. For example, the support diagnosis function 37c may update the imaging plan with the imaging condition for executing high-definition imaging in place of the imaging condition selected in advance as the imaging plan of main scanning. In other words, the support diagnosis function 37c changes the imaging plan to execute high-definition imaging only on a part detected as a lesion site without executing main scanning under the imaging condition selected in advance. Then, for example, the scan control circuitry 33 executes main scanning under the imaging condition for executing high-definition imaging in addition to the imaging condition selected in advance as the imaging plan of main scanning. Alternatively, the scan control circuitry 33 executes main scanning under the imaging condition for executing high-definition imaging in place of the imaging condition selected in advance as the imaging plan of main scanning. Alternatively, the scan control circuitry 33 executes main scanning only under the imaging condition selected in advance as the imaging plan of main scanning. In other words, the scan control circuitry 33 executes main scanning using at least one of the imaging condition selected in advance as the imaging plan of main scanning and the extracted imaging condition.

Further, when numerous parts are subjected to high-definition imaging, the support diagnosis function 37c may change the imaging plan to perform high-definition imaging in a predetermined range including the parts subjected to high-definition imaging. For example, when a plurality of lesion sites is present in the chest, the support diagnosis function 37c presents an imaging condition for changing the entire chest to high-definition imaging. In addition, when the change is accepted from the operator, the support diagnosis function 37c changes the imaging plan to capture a high-definition image of the entire chest.

In addition, the support diagnosis function 37c may determine whether to perform high-definition imaging by conventional scanning or helical scanning. More specifically, the support diagnosis function 37c determines to execute conventional scanning when the detector is 40 mm in the body axis direction and a size of the lesion site is within 40 mm, and determines to execute helical scanning when the size of the lesion site is 40 mm or more. The support diagnosis function 37c outputs a determination result to the scan control circuitry 33. In this way, the scan control circuitry 33 performs high-definition imaging by conventional scanning or helical scanning depending on the determination result.

Further, in the first embodiment described above, a description has been given on the assumption that the support diagnosis function 37c displays the imaging condition with regard to the lesion site accepted from the operator. However, the embodiment is not limited thereto. For example, the support diagnosis function 7c may automatically recommend a protocol based on a CAD result even when an instruction from the operator is not accepted. Further, a description has been given of a case in which the support diagnosis function 37c executes high-definition imaging with regard to the lesion site accepted from the operator. However, the embodiment is not limited thereto. For example, the support diagnosis function 37c may add a detected lesion site to the imaging plan even when a selection is not accepted from the operator. Further, for example, when numerous parts are subjected to high-definition imaging, the support diagnosis function 37c may change the imaging plan to perform high-definition imaging in a predetermined range including the parts subjected to high-definition imaging even when a selection is not accepted from the operator.

Second Embodiment

In the first embodiment, a description has been given of a case in which a lesion site is detected by CAD in a part set as presetting of main scanning. Incidentally, CAD automatically extracts AL to recognize a part, and is applied to each recognized part. For this reason, a lesion site detected by CAD is not limited to a preset part. In view of the above description, in a second embodiment, a description will be given of a case in which a lesion site is detected by CAD in a part other than a preset part.

A configuration of the X-ray CT apparatus according to the second embodiment is the same as the configuration of the X-ray CT apparatus 1 according to the first embodiment except that some functions of the support diagnosis function 37c are different. For this reason, a description of components other than the support diagnosis function 37c will be omitted.

Figure 13:
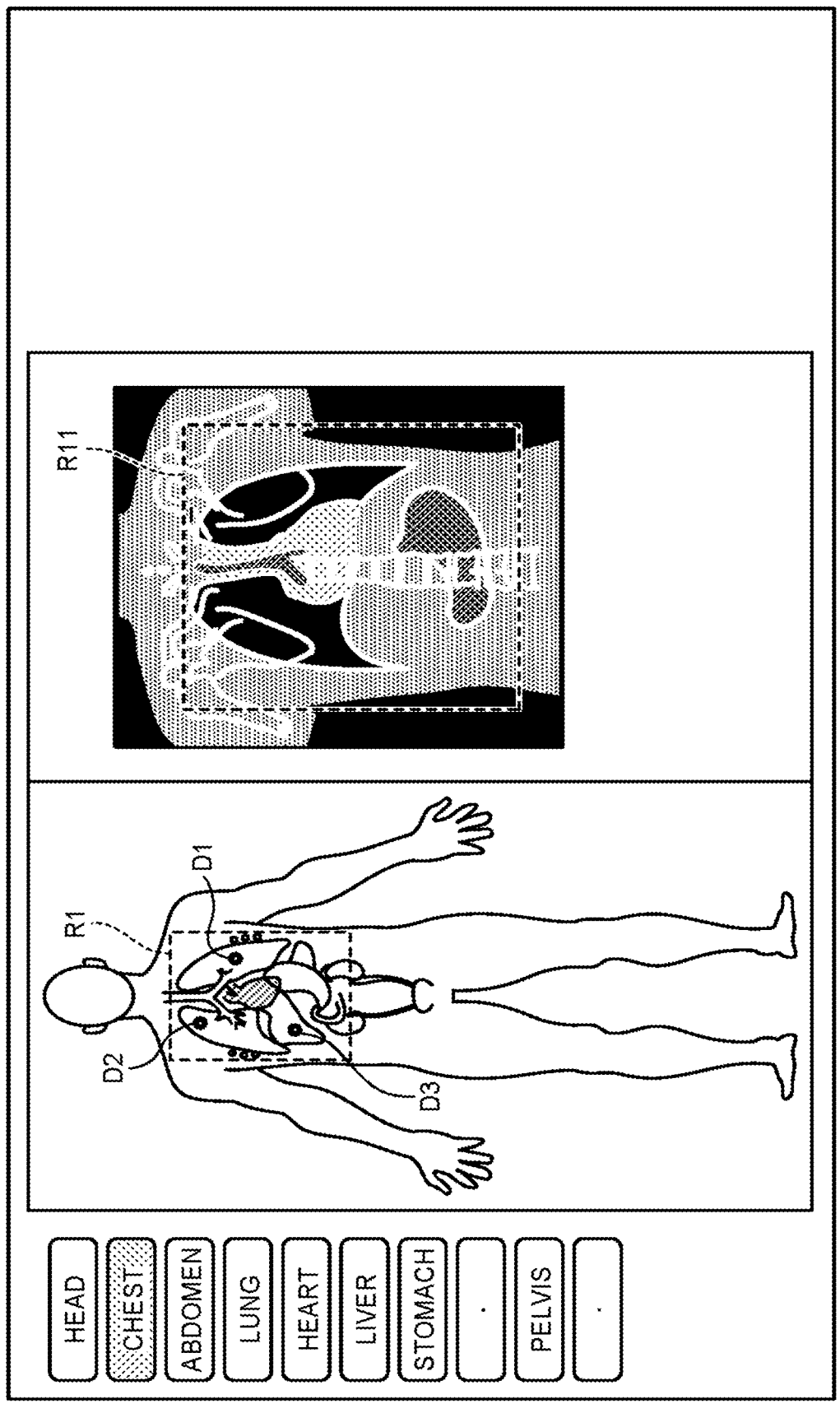
FIG. 13 is a diagram (1) for description of a second embodiment.

FIG. 13 is a diagram (1) for description of the second embodiment. Similarly to FIG. 10, FIG. 13 illustrates a GUI screen when a positioning image is captured after a chest is set as a target part in presetting. As illustrated in FIG. 13, buttons (for example, buttons of head, chest, abdomen, lung, heart, etc.) for designating a target part at the left end, a virtual patient image showing the whole human body, and a positioning image acquired by positioning scanning are displayed on the GUI screen. Further, as illustrated in FIG. 13, a processing result of diagnosis support processing is displayed on the virtual patient image.

FIG. 13 illustrates a case in which a lesion site D1 and a lesion site D2 are detected in the lung and a lesion site D3 is detected in the liver as a result of applying diagnosis support processing to a reconstructed image obtained by positioning scanning. Here, the support diagnosis function 37c corrects a display position of the result of diagnosis support processing on a virtual patient image according to a ratio between a positioning image and a virtual patient, and displays the result on the display 32. In addition, the lesion site D1 and the lesion site D2 are lesion sites specified in the lung. That is, the lesion site D1 and the lesion site D2 are lesion sites specified in the chest corresponding to a target part set by presetting. Meanwhile, the lesion site D3 is a lesion site specified in the liver. That is, the lesion site D3 is a lesion site specified in a part other than the target part set by presetting.

Figure 14:
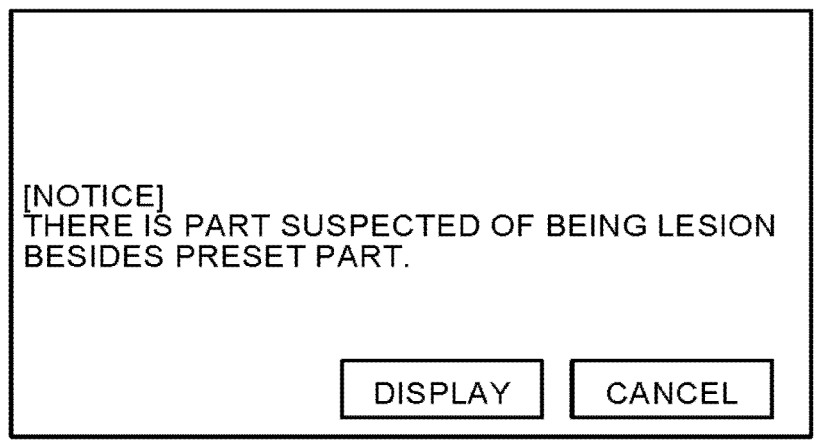
FIG. 14 is a diagram (2) for description of the second embodiment.

As illustrated in FIG. 13, it desirable to perform main scanning on a lesion site specified in a part other than the target part set by presetting in some cases. Meanwhile, there is a possibility that the operator may overlook a lesion site specified in a part other than the target part set by presetting. For this reason, the support diagnosis function 37c sets an imaging condition of main imaging with respect to a part in which a lesion site is specified out of a plurality of parts as a processing result of diagnosis support processing. For example, the support diagnosis function 37c sets an imaging condition of main scanning with respect to a part in which a lesion site is specified other than a site selected in advance as an imaging plan out of lesion sites specified as a result of diagnosis support processing. FIG. 14 is a diagram (2) for description of the second embodiment.

As illustrated in FIG. 14, for example, the support diagnosis function 37c displays a pop-up window including a notice for calling attention such as "[NOTICE] There is part suspected of being lesion besides preset part." on the display 32. In addition, as illustrated in FIG. 14, the support diagnosis function 37c displays "display" and "cancel". Here, when "cancel" is selected by the operator, the support diagnosis function 37c closes the pop-up window.

On the other hand, when "display" is selected by the operator, the support diagnosis unction 37c emphatically displays a lesion site displayed on the virtual patient and different from the preset part. For example, the support diagnosis function 37c displays the lesion site D3 illustrated in FIG. 13 in a flickering manner or using an arrow. In this way, the operator easily recognizes the lesion site D3.

In addition, when a selection of the lesion site D3 illustrated in FIG. 13 is accepted from the operator, the support diagnosis function 37c extracts a condition for executing high-definition imaging as an imaging condition for the lesion site D3, and displays a pop-up window having the same form as that of FIG. 11 on the display 32. In this way, when "cancel" is selected by the operator, the support diagnosis function 37c closes the pop-up window without adding the imaging condition of the lesion site. On the other hand, when "set" is selected by the operator, the support diagnosis function 37c adds the imaging condition displayed in the pop-up window to the imaging plan.

When the imaging condition of the lesion site is not added, the scan control circuitry 33 executes main scanning under an imaging condition selected in advance as the imaging plan of main scanning. Further, when the imaging condition of the lesion site is added, the scan control circuitry 33 executes main scanning under the imaging condition selected in advance as the imaging plan of main scanning and the extracted imaging condition. That is, when the imaging condition of the lesion site is added, the scan control circuitry 3 controls the imaging mechanism so as to perform imaging with regard to an imaging region including a part in which the lesion site is specified based on the set imaging condition.

The support diagnosis function 37c may perform diagnosis support processing on a 3D image generated by reconstructing projection data collected by main scanning, and display a processing result on the display 32. In such a case, the image reconstruction circuitry 36 generates 3D image data by reconstructing the projection data collected by main scanning. In addition, the detection function 37a detects a plurality of parts of the subject in the 3D image data. Then, the support diagnosis function 37c executes diagnosis support processing corresponding to a predetermined part with regard to a region corresponding to the predetermined part of the subject detected by the detection function 37a in the 3D image data acquired by main scanning. Then, the support diagnosis function 37c sets an imaging condition of main scanning with respect to a part in which the lesion site is specified other than a site selected in advance as the imaging plan out of lesion sites specified as a result of diagnosis support processing. In such a case, for example, the support diagnosis function 37c executes diagnosis support processing using a discrimination algorithm.

As described above, in the second embodiment, the X-ray CT apparatus 1 urges imaging of the lesion site detected by diagnosis support processing other than the preset part. For example, when a chest is set as a target part, positioning scanning is taken from a neck to an abdomen, and a lesion site is detected in the abdomen by diagnosis support processing, the X-ray CT apparatus 1 displays a notice for calling attention such that an image of the abdomen is captured. In this way, according to the second embodiment, it is possible to diagnose a lesion site detected in a site other than the target part set by presetting without overlooking the lesion site.

Even when a change in imaging plan is not accepted from the operator, the support diagnosis function 37c may change the imaging plan to execute main scanning on a specified lesion site other than a target part set by presetting.

Other Embodiments

Even though the first and second embodiments have been described far, implementation may be made in various different forms in addition to the above-described first and second embodiments.

In the above-described embodiments, a description has been given on the assumption that the support diagnosis function 37c displays a processing result of diagnosis support processing on the virtual patient. However, the embodiments are not limited thereto. For example, the support diagnosis function 37c may display the processing result of diagnosis support processing on a positioning image.

Further, the support diagnosis function 37c may request an attending physician to add an imaging instruction from a processing result of CAD. For example, the support diagnosis function 37c generates an Email urging approval of the chance in imaging plan and transmits the Email to the attending physician. Alternatively, the support diagnosis function 37c gets in touch with in-hospital extension etc. of the attending physician to urge approval of the change in imaging plan.

Further, in the above-described embodiments, a description has been given of a case in which diagnosis support processing is executed on a 3D positioning image. However, the embodiments are not limited thereto. For example, 2D CAD may be applied to a 2D positioning image.

Further, the support diagnosis function 37c may perform a control operation to output evaluation information with respect to a part of a subject detected by the detection function 37a. For example, when the detected part corresponds to the heart, the support diagnosis function 37c displays evaluation information based on a calcium score for quantitatively evaluating calcification of a coronary artery. In such a case, the support diagnosis function 37c calculates a calcium score based on a CT value. Then, the support diagnosis function 37c displays evaluation information based on the calculated calcium score. As an example, when the calcium score exceeds "600", the support diagnosis function 37c displays a warning with respect to execution of cardiac CT (coronary artery CT). In this way, an observer may determine that the cardiac CT is not appropriate as an examination for a target subject.

Further, for example, the X-ray CT apparatus 1 may save a result of diagnosis support processing with respect to a positioning image or a result of diagnosis support processing with respect to a 3D image generated by reconstructing projection data collected by main scanning in the HIS or the RIS. Then, the X-ray CT apparatus 1 uses the processing result saved as a comparison target at the time of subsequent imaging. For example, the X-ray CT apparatus 1 compares and displays a previous processing result after positioning scanning. In addition, the X-ray CT apparatus 1 may display the processing result on the virtual patient or may display the processing result on the positioning image. Further, the X-ray CT apparatus 1 may output the processing result to an external device.

In addition, when there is only one side of the kidney or lung as a result of AL analysis, there is a difference from a standard human body model. In such a case, the X-ray CT apparatus 1 displays the fact that an organ is missing on the virtual patient in a recognizable state. For example, the missing organ is painted out or an annotation is assigned thereto. Alternatively, the support diagnosis function 37c may exclude the missing organ from being subjected to diagnosis support processing.

Further, when it is determined that a foreign material such as metal is present in a part which is nut collated with an organ in the virtual patient as a result of AL analysis, the X-ray CT apparatus 1 presents existence of metal in the part on the virtual patient. For example, the fact that the foreign material corresponds to metal may be determined using a CT value. In such a case, the support diagnosis function 37c may exclude the part having the foreign material from being subjected to diagnosis support processing. In addition, when the existence of the foreign material such as metal is presented, the X-ray CT apparatus 1 may prevent the dose from being increased too much at the time of imaging, and apply metal removal reconstruction only to the part having the foreign material such as metal at the time of reconstruction. In addition, the X-ray CT apparatus 1 may display a necessary reconstruction range. For example, the X-ray CT apparatus 1 strongly applies noise removal to a large part of the subject. The part having the foreign material such as metal may be displayed on an MPR image or an axial image instead of on the virtual patient.

Further, in the X-ray CT apparatus 1, when an organ is abnormally enlarged, small, or meandering, a difference occurs from a standard human body model. In such a case, the X-ray CT apparatus 1 displays a part having a difference from the standard human body model on the virtual patient in a recognizable state. For example, the X-ray CT apparatus 1 displays a part having a difference in an organ in a flickering manner, assigns an annotation such that a symptom such as cardiac hypertrophy is recognizable, illuminates and displays a whole meandering organ, or displays a meandering place using an arrow. Further, the X-ray CT apparatus 1 may register a different one from the standard model in the HIS or the RIS, and refer to the registered one in a subsequent examination.

In the above-described embodiments, a description has been given on the assumption that the detection function 37a executes AL analysis using volume data of a positioning image or volume data of an image used for diagnosis. However, the embodiments are not limited thereto. For example, the detection function 37a may perform AL analysis using a 2D positioning image.

Figure 15:
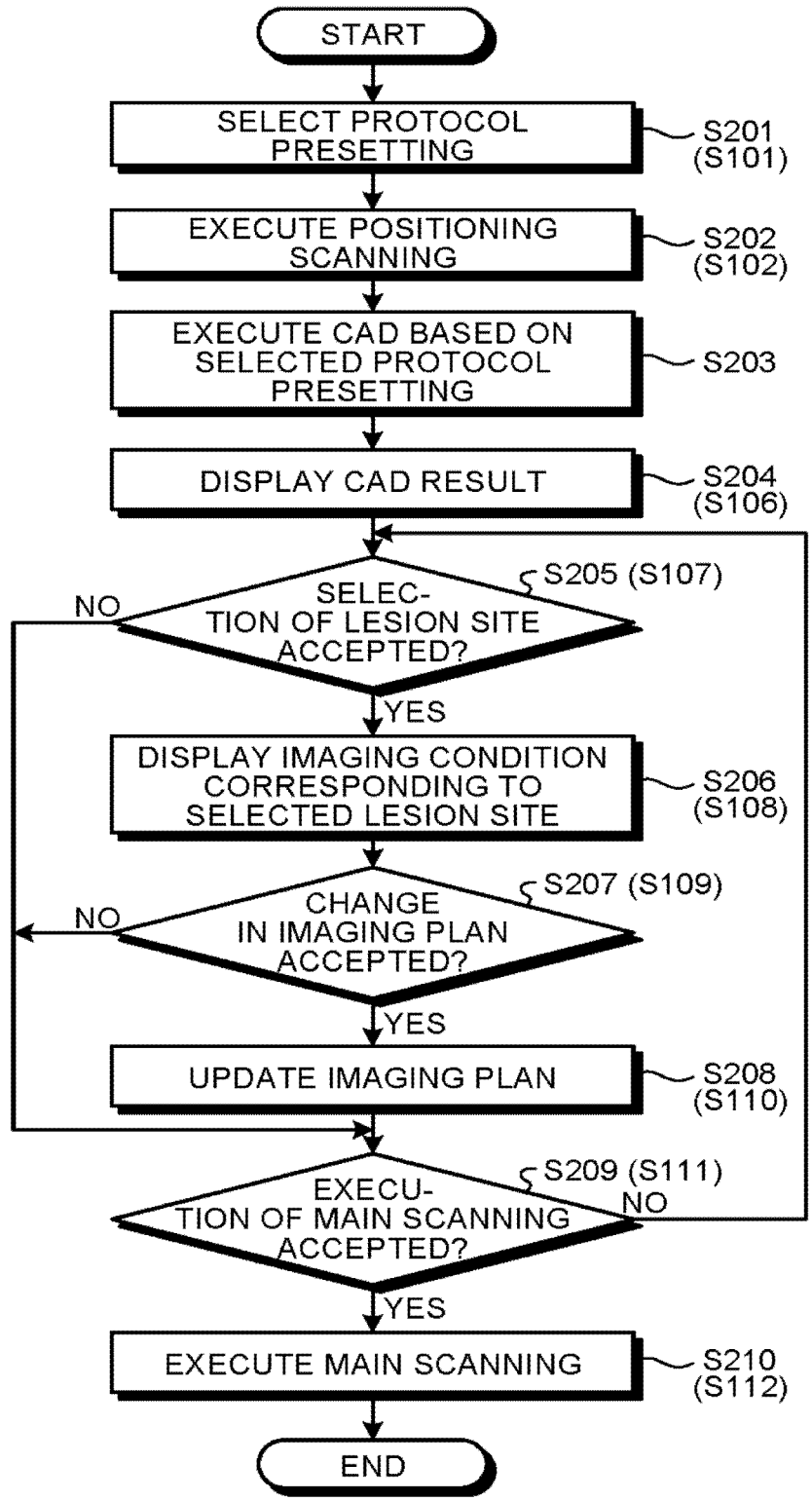
FIG. 15 is a flowchart illustrating a processing procedure by an X-ray CT apparatus according to another embodiment.

In addition, in the above-described embodiments, a description has been given on the assumption that diagnosis support processing is executed for each part of a subject detected by executing AL analysis. However, the embodiments are not limited thereto. For example, the support diagnosis function 37c may execute diagnosis support processing on image data. FIG. 15 is a flowchart illustrating processing procedure by an X-ray CT apparatus according to another embodiment.

FIG. 15 is a flowchart for description of an operation of the entire X-ray CT apparatus 1, and it is described which step of the flowchart each component corresponds to. In FIG. 15, processes similar to those in the flowchart illustrated in FIG. 12 are denoted by the same reference numerals, and a detailed description thereof will be omitted. A process of step S201 illustrated in FIG. 15 corresponds to a process of step S101 illustrated in FIG. 12, and a process of step S202 illustrated in FIG. 15 corresponds to a process of step S102 illustrated in FIG. 12.

Step S203 is a step corresponding to the support diagnosis function 37c, and is a step in which the support diagnosis function 37c is implemented when the processing circuitry 37 calls a predetermined program corresponding to the support diagnosis function 7c from the memory circuitry 35, and executes the program. In step S203, the support diagnosis function 37c executes CAD based on protocol presetting selected in step S201. Here, in step S201, when "abdomen" is selected as a "part" by protocol presetting, the support diagnosis function 37c executes CAD for the abdomen.

Processes from step S204 to step S210 illustrated in FIG. 15 correspond to processes from step S106 to step S112 illustrated in FIG. 12. In more detail, the support diagnosis function 37c sets an imaging condition of main imaging with respect to a part in which a lesion site is specified as a processing result of CAD. Then, the scan control circuitry 3 controls the imaging mechanism to perform imaging with regard to an imaging region including the part in which the lesion site is specified based on the imagine condition.

In FIG. 15, a description has been given of a case in which CAD is executed based on protocol presetting in step S203. However, the embodiments are not limited thereto. For example, the support diagnosis function 37c may accept a selection of a part for which CAD is executed from the operator in step S203. Then, the support diagnosis function 37c executes CAD corresponding to the part selected by the operator.

Alternatively, the support diagnosis function 37c may execute all CADs for respective parts held by the X-ray CT apparatus 1. For example, when the X-ray CT apparatus has CAD for the chest, CAD for the abdomen, and CAD for the pelvis, the support diagnosis function 37c executes CAD for the chest, CAD for the abdomen, and CAD for the pelvis in step S203 without considering protocol presetting set in step S201.

Furthermore, the support diagnosis function 37c may be configured to perform subdivided CAD for each part or disease. For example, when the X-ray CT apparatus 1 has CADs subdivided for each organ such as CAD for liver, CAD for large intestine, etc. or CADs subdivided for each disease such as CAD for lung cancer, CAD for breast cancer, etc. as CADs for abdomen, the support diagnosis function 37c may execute the subdivided CADs. In such a case, the support diagnosis function 37c may execute CAD based on protocol presetting. For example, when "abdomen" and "liver" are selected as "parts" by protocol presetting in step S201, the support diagnosis function 37c executes CAD for the liver. Alternatively, for example, even when "abdomen" and "liver" are selected as "parts" by protocol presetting in step S201, the support diagnosis function 37c may execute all CADs subdivided for the abdomen. The support diagnosis function 37c may execute CAD, a selection of which is accepted from the operator, or execute all CADs included in the X-ray CT apparatus 1 without considering protocol presetting.

In addition, in step S203, for example, the support diagnosis function 37c may accept a designation of an area for executing CAD in an image from the operator. Further, for example, when an imaging direction in a subject can be specified in advance as a head-to-tail direction, etc., the support diagnosis function 37c may estimate a part based on a scan distance, and execute CAD for the estimated part.

In addition, in the above-described embodiments, the X-ray CT apparatus has been described as an example of a medical image capturing apparatus. However, the embodiments are not limited thereto. For example, the medical image capturing apparatus may correspond to an X-ray diagnostic apparatus, an ultrasonic diagnostic apparatus, an MRI (Magnetic Resonance Imaging) apparatus, etc.

In addition, in the above-described embodiments, a description has been given on the assumption that diagnosis support processing is executed in the medical image capturing apparatus. However, the embodiments are not limited thereto. For example, a medical image processing apparatus, etc. may be provided as a management apparatus, and diagnosis support processing may be executed in the management apparatus. In more detail, the management apparatus acquires image data of a subject generated in the medical image capturing apparatus. Then, the management apparatus detects each of a plurality of parts of the subject in the image data generated as a positioning image. Subsequently, with regard to a region corresponding to a predetermined detected part of the subject in the image data, the management apparatus executes diagnosis support processing corresponding to the predetermined part. Further, the management apparatus sets an imaging condition of main imaging with respect to a part in which a lesion site is specified among a plurality of parts as a processing result of diagnosis support processing. Then, the management apparatus instructs the medical image capturing apparatus to perform imaging with regard to an imaging region including the part in which the lesion site is specified based on the imaging condition.

Alternatively, the management apparatus acquires the image data of the subject generated in the medical image capturing apparatus. Then, the management apparatus executes diagnosis support processing with respect to the image data. Further, the management apparatus sets an imaging condition of main imaging with respect to a part in which a lesion site is specified as a processing result of diagnosis support processing. Then, the management apparatus instructs the medical image capturing apparatus to perform imaging with regard to an imaging region including the part in which the lesion site is specified based on the imaging condition.

In addition, diagnosis support processing may be distributed and executed in the medical image capturing apparatus and the management apparatus. For example, the medical image capturing apparatus performs a process of generating image data of a subject. The management apparatus performs a process of acquiring the image data of the subject generated in the medical image capturing apparatus, and performs a process of detecting each of a plurality of parts of the subject in the image data generated as a positioning image. Subsequently, with regard to a region corresponding to a predetermined detected part of the subject in the image data, the management apparatus executes diagnosis support processing corresponding to the predetermined part. Further, the management apparatus performs a process of setting an imaging condition of main imaging with respect to a part in which a lesion site is specified among a plurality of parts as a processing result of diagnosis support processing. Then, the medical image capturing apparatus performs a process of controlling the imaging mechanism to perform imaging with regard to an imaging region including the part in which the lesion site is specified based on the imaging condition.

Alternatively, for example, the medical image capturing apparatus performs a process of generating image data of a subject. The management apparatus executes diagnosis support processing on the image data. Further, the management apparatus performs a process of setting an imaging condition of main imaging with respect to a part in which a lesion site is specified as a processing result of diagnosis support processing. Then, the medical image capturing apparatus performs a process of controlling the imaging mechanism to perform imaging with regard to an imaging region including the part in which the lesion site is specified based on the imaging condition.

In the above-described embodiments, the medical image processing apparatus has been described as an example of the management apparatus. However, the embodiments are not limited thereto. For example, the console 30 of the X-ray CT apparatus 1 may be used as the management apparatus. Alternatively, for example, an apparatus connecting a plurality of medical image capturing apparatuses may be used as the management apparatus. In addition, a process in the management apparatus may be implemented in cloud computing.

For example, the term "processor" used in the above description may refer to a CPU (Central Processing Unit), a GPU (Graphics Processing Unit), or a circuit such as an application specific integrated circuit (ASIC), a programmable logic device (for example, a simple programmable logic device (SPLD), a complex programmable logic device (CPLD), and a field programmable gate array (FPGA)), etc. The processor implements a function by reading a program saved in the memory circuitry and executing the program. Instead of saving the program in the memory circuitry, the program may be directly incorporated in a circuit of the processor. In this case, the processor implements a function by reading a program incorporated in the circuit and executing the program. Each processor of the present embodiment may not be configured as a single circuit for each processor. A plurality of independent circuits may be combined to form a single processor, and a function thereof may be implemented. Further, a plurality of components in FIG. 2 may be integrated into one processor to implement a function thereof.

In addition, each component of each device illustrated in the above embodiment corresponds to a functional concept, and may not be physically configured as illustrated. In other words, specific forms of distribution/integration of each device are not limited to those illustrated in the figure, and all or some forms may be functionally or physically distributed/integrated in arbitrary units according to various loads, usage conditions, etc. Furthermore, all or an arbitrary part of each processing function performed in each device may be implemented by a CPU and a program analyzed and executed by the CPU, or may be implemented as hardware by wired logic.

Further, a control method described in the first embodiment may be implemented by executing a control program prepared in advance by a computer such as a personal computer, a workstation, etc. This control program may be distributed via a network such as the Internet. Further, this control program may be implemented by being recorded on a computer readable recording medium such as a hard disk, a flexible disk (FD), a CD-ROM, an MO, a DVD, etc. and being read from the recording medium by a computer.

As described above, according to each embodiment, it is possible to optimize an imaging condition of main scanning with reference to a processing result of support diagnosis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image capturing apparatus comprising:
    image generation circuitry configured to generate three-dimensional (3D) image data of a subject by reconstructing projection data collected by main scanning;
    detection circuitry configured to detect each of a plurality of parts of the subject in the 3D image data generated as a positioning image;
    diagnosis support processing circuitry configured to execute diagnosis support processing corresponding to a predetermined part with regard to a region corresponding to the predetermined part of the subject detected by the detection circuitry in the 3D image data acquired by the main scanning;
    setting circuitry configured to set an imaging condition of main imaging with respect to a part in which a lesion site is specified among the plurality of parts as a processing result of the diagnosis support processing circuitry; and
    imaging control circuitry configured to control an imaging mechanism to perform imaging with regard to an imaging region including the part in which the lesion site is specified based on the imaging condition.

2. The medical image capturing apparatus according to claim 1, wherein the setting circuitry sets an imaging condition of main scanning with respect to a part in which a lesion site selected by an operator is specified among lesion sites specified as a result of the diagnosis support processing.

3. The medical image capturing apparatus according to claim 1, wherein the setting circuitry sets an imaging condition of main scanning with respect to a part in which a lesion site is selected other than a site selected in advance as an imaging plan among lesion sites specified as a result of the diagnosis support processing.

4. The medical image capturing apparatus according to claim 1, wherein the setting circuitry sets a condition for executing high-definition imaging as the imaging condition.

5. The medical image capturing apparatus according to claim 4, wherein the setting circuitry sets at least one of a tube voltage, a tube current, an imaging range, and a reconstruction condition as the condition for executing the high-definition imaging.

6. The medical image capturing apparatus according to claim 1, wherein the diagnosis support processing circuitry causes a display to display the processing result.

7. The medical image capturing apparatus according to claim 6, wherein the diagnosis support processing circuitry causes the display to display the processing result in a display form corresponding to an importance.

8. The medical image capturing apparatus according to claim 6, wherein the diagnosis support processing circuitry causes the display to display the processing result on a virtual patient associated with each part of the subject.

9. The medical image capturing apparatus according to claim 8, wherein the diagnosis support processing circuitry corrects a display position of the processing result according to a ratio between the positioning image and the virtual patient, and causes the display to display the result.

10. The medical image capturing apparatus according to claim 6, wherein the diagnosis support processing circuitry causes the display to display the processing result on the positioning image.

11. A method comprising:
    generating 3D image data of a subject by reconstructing projection data collected by main scanning;
    detecting each of a plurality of parts of the subject in the 3D image data acquired as a positioning image;
    executing diagnosis support processing corresponding to a predetermined part with regard to a region corresponding to the predetermined part of the subject detected in the 3D image data acquired by the main scanning;
    setting an imaging condition of main imaging with respect to a part in which a lesion site is specified among the plurality of parts as a processing result of the diagnosis support processing; and
    controlling an imaging mechanism to perform imaging with regard to an imaging region including the part in which the lesion site is specified based on the imaging condition.

12. The method according to claim 11, wherein the setting step sets an imaging condition of main scanning with respect to a part in which a lesion site selected by an operator is specified among lesion sites specified as a result of the diagnosis support processing.

13. The method according to claim 11, wherein the setting step sets an imaging condition of main scanning with respect to a part in which a lesion site is selected other than a site selected in advance as an imaging plan among lesion sites specified as a result of the diagnosis support processing.

14. The method according to claim 11, wherein the setting step sets a condition for executing high-definition imaging as the imaging condition.

15. The medical image capturing apparatus according to claim 14, wherein the setting step sets at least one of a tube voltage, a tube current, an imaging range, and a reconstruction condition as the condition for executing the high-definition imaging.

16. The method according to claim 11, wherein the executing diagnosis support processing causes a display to display the processing result.

17. The method according to claim 16, wherein the executing diagnosis support processing causes the display to display the processing result in a display form corresponding to an importance.

18. The method according to claim 16, wherein the executing diagnosis support processing causes the display to display the processing result on a virtual patient associated with each part of the subject.

19. The method according to claim 18, wherein the executing diagnosis support processing corrects a display position of the processing result according to a ratio between the positioning image and the virtual patient, and causes the display to display the result.

20. The method according to claim 16, wherein the executing diagnosis support processing causes the display to display the processing result on the positioning image.

* * * * *